(12) United States Patent
Anderson et al.

(10) Patent No.: US 6,642,019 B1
(45) Date of Patent: Nov. 4, 2003

(54) VESSEL, PREFERABLY SPHERICAL OR OBLATE SPHERICAL FOR GROWING OR CULTURING CELLS, CELLULAR AGGREGATES, TISSUES AND ORGANOIDS AND METHODS FOR USING SAME

(75) Inventors: Charles Daniel Anderson, Houston, TX (US); Charlie W. Dodd, Seabrook, TX (US); Mark Stuart Anderson, North Richland Hills, TX (US)

(73) Assignee: Synthecan, Inc., Houston, TX (US)

( * ) Notice: Subject to any disclaimer, the term of this patent is extended or adjusted under 35 U.S.C. 154(b) by 273 days.

(21) Appl. No.: 09/718,814

(22) Filed: Nov. 22, 2000

(51) Int. Cl.⁷ .............................. C12P 1/00; C12M 1/10
(52) U.S. Cl. ...................... 435/41; 435/183; 435/298.2; 435/297.1; 435/297.2; 435/286.5
(58) Field of Search ............... 435/298.2, 297.1, 435/297.2, 286.5, 41, 183

(56) References Cited

U.S. PATENT DOCUMENTS

| | | |
|---|---|---|
| 4,988,623 A | 1/1991 | Schwarz et al. |
| 5,026,650 A | 6/1991 | Schwarz et al. |
| 5,153,131 A | 10/1992 | Wolf et al. |
| 5,153,132 A | 10/1992 | Goodwin et al. |
| 5,153,133 A | 10/1992 | Schwarz et al. |
| 5,155,034 A | 10/1992 | Wolf et al. |
| 5,155,035 A | 10/1992 | Schwarz et al. |
| 5,308,764 A | 5/1994 | Goodwin et al. |
| 5,330,908 A | 7/1994 | Spaulding |
| 5,376,548 A | 12/1994 | Matsuo et al. |
| 5,437,998 A | 8/1995 | Schwarz et al. |
| 5,449,617 A | 9/1995 | Falkenberg et al. |
| 5,523,228 A | 6/1996 | Ingram et al. |
| 5,605,835 A | 2/1997 | Hu et al. |
| 5,622,857 A | 4/1997 | Goffe |
| 5,665,594 A | 9/1997 | Schwarz et al. |
| 5,688,687 A | 11/1997 | Palsson et al. |
| 5,702,941 A | 12/1997 | Schwarz |
| 5,763,279 A | 6/1998 | Schwarz et al. |
| 5,989,913 A | 11/1999 | Anderson et al. |
| 6,001,642 A | 12/1999 | Tsao |

*Primary Examiner*—James Ketter
(74) *Attorney, Agent, or Firm*—John R. Casperson; Frank S Vaden, III

(57) ABSTRACT

An improved culture vessel or bioreactor for growing cells, cellular aggregates, tissue particles or tissue "organoids" and methods for using same which includes a housing having at least one chamber defined by a curved wall symmetrical about an axis. The perfused version of the vessel has at least one inlet and at least one outlet and at least one filter in fluid communication with at least one of the inlets or outlets structured to pass culture media but retain cells, cellular aggregates or tissues within the culture chamber. The batch culture version of the vessel has at least part of the vessel wall made of a gas permeable material. The vessel housing is rotated about the horizontal or proximate horizontal axis to suspend the cells, in an unobstructed, three-dimensional or toroidal flow. The chamber has a substantially ellipsoid, oblate ellipsoid, spherical or oblate spherical shape and an unobstructed volume for growth of cells, cellular aggregates or tissues. The perfused version of the invention has a pump in fluid communication with an inlet or outlet to maintain a flow of oxygen and nutrient rich culture media through the vessel to sustain respiration and metabolism. A gas exchange device is used to maintain desired concentration of gases. Operational modes include either continuous perfusion flow or a batch culture. Methods are disclosed to produce biological products, cells and tissues and to filter waste materials and toxins from fluids (such as a liver assist device).

63 Claims, 16 Drawing Sheets

VESSEL, PREFERABLY SPHERICAL OR OBLATE SPHERICAL FOR GROWING OR CULTURING CELLS, CELLULAR AGGREGATES, TISSUES AND ORGANOIDS AND METHODS FOR USING SAME

FIELD OF THE INVENTION

This present invention relates to culture vessels, sometimes referred to as bioreactors, for growing cells, three dimensional cellular aggregates, "organoids," tissues or the like (at times referred to below as "particles") and their method of use for carrying out various cellular processes with tissues and/or organoids and for diagnostic testing and research.

BACKGROUND OF THE INVENTION

This invention relates to improvements in culture vessels for growing or culturing cells, cellular aggregates, tissues, organoids and the like and to methods for using the same, and in particular to improvements in culture vessels as disclosed in U.S. Pat. Nos. 5,989,913 and 6,080,581, issued to Charles D. Anderson on Nov. 23, 1999 and Jun. 27, 2000, respectively, both hereby incorporated herein by reference in their entirety. Both of these patents are not admitted to be prior art with respect to the present invention by their incorporation into this application.

Most prior art culture vessels have been cylindrical in shape with flat, vertical interior end walls and many prior art vessels incorporate other interior obstructions, such as central cylindrical cores, agitators or impellers, which also impact the flow paths of cells, cellular aggregates, "organoids" or tissue particles (see definition within), and are thought to create impact and/or abrasion surfaces impeding toroidal flow. U.S. Pat. No. 6,001,642 to Tsao, entitled "Bioreactor and Cell culturing Process Using the Bioreactor," discloses an asymmetrical bioreactor having one spherically-shaped wall facing and connecting to a second flat wall. This bioreactor is commonly named the Hydrodynamic Focusing Bioreactor. The center of the flat wall features a spinner type agitator that projects into the middle of the culture chamber and is designed to enhance bubble removal. The bioreactor of the '642 patent does not have a chamber defined by a smooth, non-flat, spherical, oblate spherical or curved wall that is symmetrical about an axis in that one wall of the culture chamber is essentially flat except for a centrally mounted agitator. The front and back walls of the '642 bioreactor join at a very sharp angle that would impede toroidal flow. There is an agitator in the center of the culture chamber of the '642 bioreactor that impedes toroidal flow across the center of the vessel and creates turbulence. Finally, the hydrodynamic focusing bioreactor is not intended to facilitate toroidal flow but is intended to focus the flow within the vessel into a "donut" pattern. The focusing action created by this centrally located spinner agitator causes shear, turbulence, and vessel wall impacts especially against the flat back wall of the device.

The need exists for a continuously renewed culture vessel, rotated over an essentially horizontal axis, that minimizes interior structures that impedes the ability of cells, cellular aggregates or tissues to freely expand in three dimensional growth under minimally disturbed toroidal flow. The vessel would have an inlet and an outlet in fluid communication with a pump and at least one filter in fluid communication with an outlet. There is a need for a version of such a culture vessel or bioreactor that may be operated as a batch reactor.

There is also a need for a method of use of such culture vessels or bioreactors for the production of biological products, and for the removal of toxins and biological waste from a fluid using cellular mechanism. The culture vessels or bioreactors of the present invention address these needs.

SUMMARY OF THE INVENTION

The present invention pertains to a culture vessel essentially horizontally rotatable on a horizontal axis, the vessel having at least one chamber. The chamber in one preferred embodiment has spherical, oblate, extended spherical or extended oblate spherical wall portions. Typically, though not necessarily, the chamber would be symmetrical about the longitudinal axis. The chamber has an inlet and outlet in fluid communication with at least one pump. At least one filter in the chamber passes fluid and cellular waste out the outlet while retaining the cells, tissue, organoids or the like. Also the invention relates to methods for using such a culture vessel for growing cells, cellular aggregates, organs, tissues and the like and for the production of biological products or the removing of toxins or biological waste from a fluid using cellular mechanisms.

Testing has confirmed that a culture vessel with a continuously renewing fluid medium therethrough need not be cylindrical, as is the custom in the industry. Testing shows that the chamber is not limited to a cylindrical shape, but a spherical or oblate spherical or extended spherical or extended oblate spherical shape may provide an improved shape for a culture chamber. A spherical or oblate spherical or extended spherical or extended oblate spherical shape for a chamber offers, as viewed at in cross section through a longitudinal axis, rounded corners that facilitate growth or other operative cultures by minimizing impact forces and shearing forces upon particles moving within the chambers. Such lateral movement is described below. It has further been determined that in the simplest embodiments of a culture chamber, only one filter is needed, in fluid communication with an outlet. A chamber can function adequately without the safety feature of a second upstream filter, although the ability to reverse flow between a chamber inlet and outlet would be sacrificed. Upstream valving could be employed, in lieu of an upstream filter to protect against cell migration through an inlet.

As disclosed in the referenced and incorporated patents above, particles continuously descend or sediment through a culture fluid in a vessel horizontally rotated about a longitudinal axis. While it had been thought that particles in such circumstances descend in a linear or two-dimensional flow path and were uniformly distributed in the horizontally rotated culture vessel, it has been observed that distinct or visible bands of particles are formed in such rotated vessels. The flow path is three-dimensional. Particles migrate along toroidal, three dimensional flow paths. Surmise is that such toroidal flow may be due in part to Coriolis forces acting on the particles as they move inside of the rotated vessel.

The phrase, "toroidal flow" indicates that the particles do not simply rotate in a simple circular pattern with the chamber fluid about an essentially horizontal longitudinal chamber axis. If the end point of a particle at the end of a full 360 degree rotation about a longitudinal axis could be plotted, the following would be apparently detected. A cross section taken through the longitudinal axis would show the end point migrating in a small circle over time, in the plane of the cross section, traversing a portion of the circumference of that circle with each 360 degree revolution around the horizontal axis. A cross section taken normal to the longitudinal axis would show the end point migrating in another small circle in the plane of the cross section, traversing a segment of the circumference of that circle, with each 360 degree rotation. The path of a particle would appear to describe a three dimensional sphere or egg shape over time.

Growth of cells, cellular aggregates, organoids or tissues and the like may be increased and enhanced to the extent the cells, cellular aggregates, organoids or tissues are permitted to freely expand in three dimensions while remaining undisturbed in toroidal flow ,as described above.

Observation of particle motion in horizontally rotated bioreactors indicates that natural toroidal flow is disturbed when the particles collide or have impact with interior walls (and/or any other obstructions within a vessel). The violence of the impact affects growth. Reduced shearing forces and/or reduced number of impacts with interior walls facilitates undisturbed motion and results in faster cellular growth, larger sized cellular aggregates or tissues, more efficient removal of toxins and biological wastes and the enhanced secretion of desired bioproducts.

The geometry of the interior of a rotated culture vessel can be a factor in decreasing the number of vessel wall impacts and/or shearing forces of impact. Culture vessels having spherical, oblate spherical, extended spherical and/or extended oblate spherical wall portions or viewed by cross section through a longitudinal axis, are conducive to minimizing shearing forces and/or the number of vessel wall impacts. A reduced angle of impact should result in lower shearing forces. Lower shearing forces should result in less transferred momentum. Reduced shearing forces and number of impacts by culture vessels having spherical, oblate spherical, extended spherical and/or extended oblate spherical wall portions thus should cause less of a departure from normal toroidal flow for growing cells, cellular aggregates and tissues. In fact, vessels having spherical, oblate spherical, extended spherical or extended oblate spherical walls have been shown to produce faster cell growth and to produce larger size aggregates or tissues than what has been achieved in prior art vessels having substantial flat interior end walls or surfaces than what has been achieved in prior art vessels having substantially flat interior end walls or surfaces and cylindrical bodies.

The present invention is directed to a horizontally rotatable culture vessel or bioreactor that has smooth, curved, spherical, oblate spherical, non-flat walls for growing cells, cellular aggregates, tissue particles or "organoids" and a method for use of such vessel or bioreactor. A preferred embodiment of the invention is a culture vessel which includes a housing having a chamber defined by a spherical, oblate spherical or curved wall symmetrical about an axis, an inlet and an outlet. One embodiment of such a vessel also includes at least one filter in fluid communication with at least one of the inlets and outlets, the filter structured to pass culture media and cellular waste and to retain cells, cellular aggregates or tissues and a means for rotating the culture vessel about its proximate horizontal axis. This filter version will include a pump in fluid communication with the inlet or outlet, to flow the culture media through the vessel and a method of transferring dissolved gases into and out of the culture media. The gas exchange device will be exterior to the culture vessel but will be in fluid communication with the culture vessel. The vessel or bioreactor will be rotated about a substantially horizontal axis.

The other version of the spherical, oblate spherical, extended spherical, extended oblate spherical or curved wall vessel will be a batch culture device. The batch culture device will have a gas permeable membrane within the housing. In some embodiments, at least part of the wall of this vessel will be made of a gas permeable material. The culture media in the batch culture device will be changed by stopping the rotation of the vessel and removing and replacing a given amount of culture medium as a batch. Typically approximately ⅓ culture medium is retained and is known in the art as "conditioned medium", approximately ⅔ of fresh medium is added. After the culture medium has been changed in this manner, rotation will be resumed. The gas permeable batch culture device is a low cost, short duration alternative to the continuous perfused system. This system may be used for chemotherapy testing, perhaps 5 to 10 different vessels would have cells grown with cancer cells taken from the patient. A physician may then test various modalities of treatment on the different batch vessels to determine which would have the greatest measure of success in the patient. This system could be built as a disposable or reusable device.

The culture vessel or bioreactor of the present invention may be used to grow cells, cellular aggregates, tissue or tissue "organoids" in a continuous manner or versions of the invention will operate as batch culture devices. In the batch culture version, at least part of the smooth, curved, spherical, oblate spherical, non-flat vessel wall will be constructed of gas permeable material.

The filter or filters of the perfused culture vessel or bioreactor of the present invention may be disposed about a chamber of the housing in one or more preferred embodiments. A filter or filters may be located proximate an axis of rotation, or an inlet or outlet or both. The filter or filters may be disposed about at least one chamber defined by a curved wall. In addition, a filter may enclose cells, cellular aggregates or tissues in at least one chamber of the housing. The filter or filters may be structured to pass culture media and waste from an inlet while retaining cells, cellular aggregates, "organoids" or tissues. The filter may also be structured to pass culture media from the outlet to the inlet while retaining such cells.

In any of the preferred embodiments of the culture vessel or bioreactor of this invention, at least a portion of the chamber may have a substantially curved, ellipsoid, oblate ellipsoid, spherical, extended spherical, oblate spherical or extended oblate spherical shape. Further, one or more of the preferred embodiments of this invention may include means for removing bubbles from the media such as a recession for trapping bubbles in the chamber and a port for releasing the trapped bubbles. Also, a gas exchange device and means for monitoring temperature, pressure or PH of the chamber may be included. When the vessel is operated in a continues manner, means for monitoring the culture media flow rate may also be included.

Another embodiment of the invention is a method for growing or maintaining cells, cellular aggregates or tissue particles or "organoids". The method includes introducing living cells, cellular aggregates, "organoids" or tissue material into a culture media in a vessel chamber having a spherical or oblate spherical or continuos curved wall symmetrically about an axis, an inlet and an outlet. In the perfusion version of the invention the chamber has at least one filter, typically two filters, an inlet filter and an outlet filter in fluid communication with the inlet or outlet and structured to pass culture media and cellular waste and to retain cells, cellular aggregates or tissues. The cells, cellular aggregates or tissues are suspended by rotating the vessel about its horizontal axis. The method may further include reversing the flow of the culture medium through the vessel in a continuos manner to use the outlet filter as an inlet to unclog and remove debris from the outlet filter and to increase filter life by using the inlet filter as an outlet filter. A typical type of debris would be material that clogs filters such as mucin produced by the cells, cellular aggregates, "organoids" or tissue materials. In the batch culture version at least part of the surface of the vessel is made up of gas permeable material so that the cells, cellular aggregates, "organoids" or tissue materials are provided dissolved oxygen and the metabolic dissolved carbon dioxide is removed from the culture vessel. Expended media is removed from the batch culture vessels by stopping the vessel, withdrawing a given amount of expended media and replacing it with a fresh batch of media. This process was explained in more detail above. In order to maintain a sterile environment, these procedures are performed under a sterile hood, which maintains a clean environment.

Either the perfused or the batch culture version may be used to produce biological products from the growth or maintenance of cells or tissues. An example of such a method of use would be the production of human hormones, enzymes or protein pharmaceuticals.

Still another embodiment of this invention is a method for producing desired biological products into or removing toxins or biological waste material from a circulating fluid using cellular mechanisms. The method includes establishing a culture of live cells or organoids in a culture fluid in a chamber that has a spherical or oblate spherical; or continuous curved wall symmetrically about an axis. Fluid containing waste material is added to the vessel containing the culture of cells, cellular aggregates, "organoids" or tissue materials, having a chamber defined by as spherical, oblate or extended curved wall symmetrical about an axis, an inlet and an outlet. Oxygen and nutrients are provided to the organoids. The cells or organoids are suspended by rotating the vessels about its horizontal axis. Multiple vessels may be connected in series. When the first vessel in the series becomes spent, it is removed and a fresh vessel is added to the other end of the series. The toxins or waste materials are removed from the fluid using the cellular metabolic mechanisms of the organoids. An example of such a device would be a "Liver Assist Device" which would use liver cells or tissue cultures in this invention to detoxify blood plasma that would be reinfused into the patient. An example of the use of the invention to produce a desired biological product would use pancreatic islets to produce insulin into the patients plasma that would be reinfused into the patient.

BRIEF DESCRIPTION OF THE DRAWINGS

So that the manner in which the above-recited features, advantages and objects of the invention are attained, as well as others which will become apparent, and can be understood in detail. More particular description of the invention briefly summarized above may be had by reference to the exemplary preferred embodiments thereof which are illustrated in the appended drawings, which form a part of this specification. It is to be noted, however, that the drawing illustrate only typical preferred embodiments of the invention and are therefore not to be considered limiting of its scope as the invention may admit to other equally effective embodiments.

In the Drawings.

DESCRIPTION OF THE PREFERRED EMBODIMENTS

The present invention and preferred embodiments thereof may be better interpreted by reference to drawings and the detailed description.

"Substantially horizontal" is intended to mean an axis that deviates no more than 20 degrees from a horizontal axis, and preferably, an axis that deviates no more than 10 degrees from said horizontal axis, and more preferably, an axis that is the horizontal axis.

"Major Axis," when used in the context of describing the axis of rotation of a culture vessel or bioreactor having a chamber portion substantially spherical, elliptical, oblate elliptical or rounded oblate shape is intended to mean, an axis no more than about 20 degrees from the approximate horizontal axis of such chamber portion, and preferably, an axis no more than 10 degrees from said approximate horizontal axis, and more preferably, an axis is the approximate horizontal axis of an ellipse, oblate ellipse or rounded oblate chamber portion.

"Axis," when used in the context of describing the axis of rotation of a culture vessel or bioreactor having a chamber portion substantially spherical or oblate spherical shape is intended to mean an axis no more than about 20 degrees from the axis of such chamber portion, preferably, an axis no more than 10 degrees from said axis, and more preferably, an axis that is the horizontal axis of a spherical or oblate spherical chamber portion.

Figure 1:
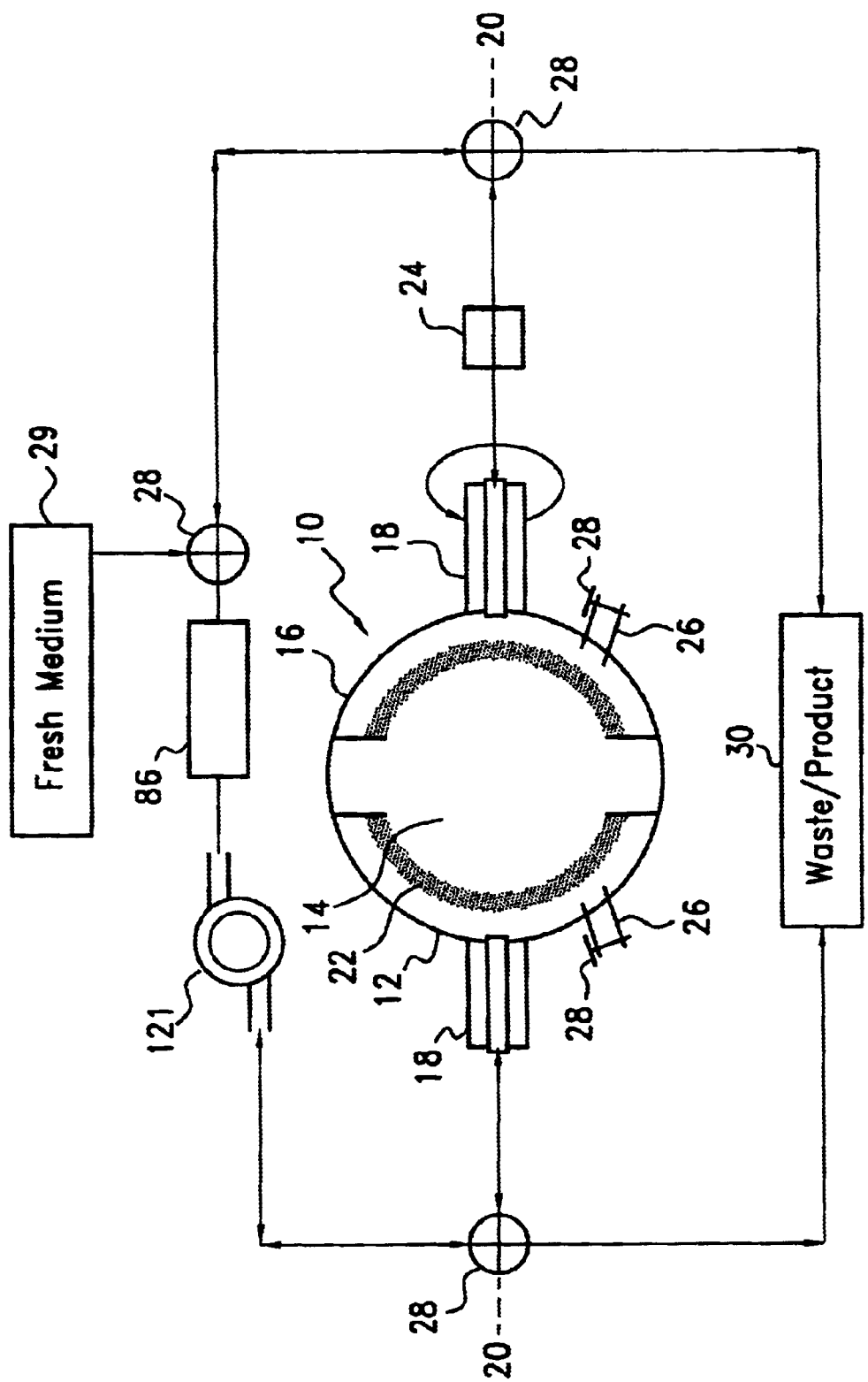
FIG. 1 is a cross sectional view of a spherical culture vessel or bioreactor of in a perfused system having a chamber defined by a curved wall symmetrical about an axis and a housing that may be rotated about a substantially major horizontal axis.

Referring now to the drawings, FIG. 1 shows the general organization of a preferred embodiment of a perfused culture vessel 10 or bioreactor 10 of the present invention. A housing 12 having at least one chamber 14 defined by a curved wall 16 symmetrical about a substantially horizontal axis 20. The culture vessel 10 has at least one filter 22 in fluid communication with at least one inlet/outlet port 18, such filter 22 is preferably located proximate an axis. Filter 22 may be structured to pass culture media and cellular waste and to retain cells, cellular aggregates or tissues. Housing 12 of vessel 10 has a means (not shown) for rotating the vessel 10 via coupling means 24 that is not in fluid communication with inlet/outlet ports 18, however the inlet/outlet ports 18 that are carried by the gasket coupling means 24 are in fluid communication with the vessel. The vessel may have an access port 26. Rotation will be around the substantially horizontal axis 20. Preferably, such rotating means may be a drive motor or the like. It is envisioned that vessel 10 may have a plurality of inlet/outlet ports 18 in fluid communication with at least one chamber.

Fresh culture media 29 from a tank or other supply source flows through conduit C to valve 28 where it is directed to at least one of the inlet/outlet ports of culture vessel 10. Culture media, providing nutrients and oxygen to the growing cells, cellular aggregates and tissues in the chamber 14, any enter such chamber 14 through inlet/outlet ports 18 and filter 22 that is in fluid communication with such inlet/outlet ports 18. When culture vessel 10 has a filter 22 in fluid communication with one or more inlet/outlet ports, the culture media containing cellular wastes may also be removed through such ports 18. The waste-containing media flows through conduit C to valves 28 and to waste media tank 30. Valves 28 may be a three-way valve structured to flow fluid from fresh media tank 29 through the culture vessel 10 to waste tank 30. Alternatively, valves 28 may be operated to flow fluid in the reversed direction from the fresh media tank 29 through the culture vessel 10 to the waste media tank, thus reversing the flow through the culture chamber. A pump 121 is typically used to provide means for fluid flow. A particular type of pump, a peristaltic pump is typically used in this type of application. As is shown in FIG. 1, the oxygenator 86 is hooked up to the pump 121 at one end and the rotating coupling 24 at the other end. It is clear that oxygen rich fluid is entering into the culture chamber.

Filters 22 may become clogged periodically with cells, cellular aggregates or tissue and/or waste materials. If this should occur, such filters 22 may be cleared by reversing the direction of culture media flow, referring again to FIG. 1, for example, vessel 10 may be supplied with culture media flowing from a first filter 22, shown on the left of FIG. 1, through the chamber to a second filter 22, shown on the right of FIG. 1. Growing cells, cellular aggregates or tissues and/or waste may clog the filters during the operation of the vessel 10. To clear the filter, culture media flow may be reversed to flow from the second filter 22 through the culture chamber to first filter 22. Filters 22 may be structured to pass culture media and cellular waste and to retain cells, cellular aggregates or tissues when flowing media from the first filter to the second filter or in the reverse direction from the second filter to the first filter. Also, the direction of flow of culture media may be reversed in order to cause the suspended cells, cellular aggregates or tissues to become attached to a substrate of the filter elements of the vessel 10. Filter 22 may be fabricated of any suitable material, preferably such filter 22 may be fabricated from cloth, metal or plastic.

The figures show alternative preferred embodiments of culture vessel or bioreactor 10 of the present invention. The axis of rotation 20 is substantially horizontal in all figures. Similar reference numerals are used for ease of understanding in several different embodiments of the various shapes of the culture vessel. Two basic modes of operation are perfused, thus having a filter, and batch, thus having a gas permeable membrane g.

Figure 2:
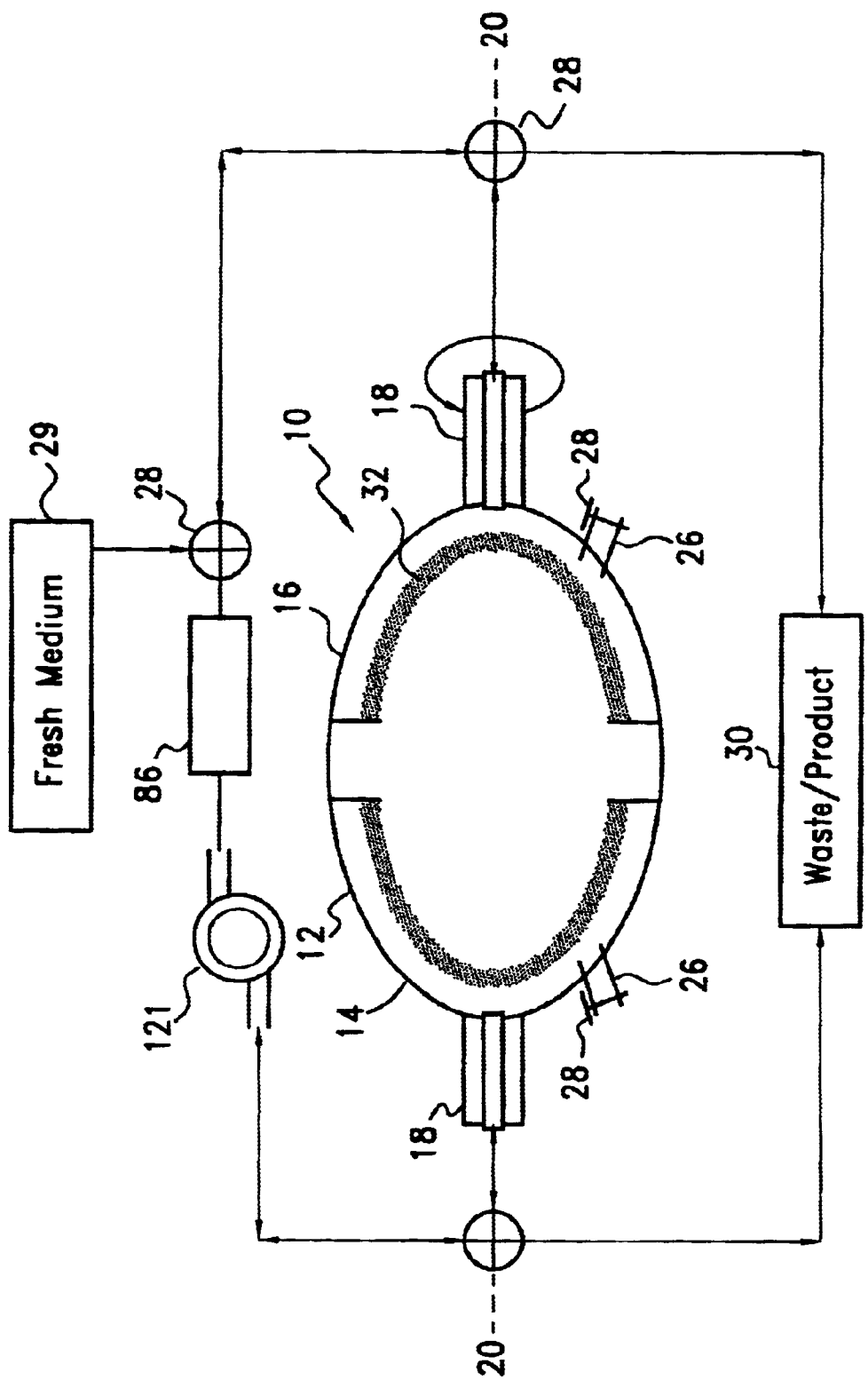
FIG. 2 is a cross sectional view of a oblate ellipsoid culture vessel or bioreactor having a filter disposed about a curved chamber wall. The perfused system with pump and oxygenator is shown.

FIG. 2 is an embodiment of culture vessel 10 wherein a portion of chamber 14 is shown having substantially ellipsoid shape and having at least one filter 32 disposed about curved wall 16. Housing 12 may be rotated around a substantially horizontal major axis 20.

Figure 3:
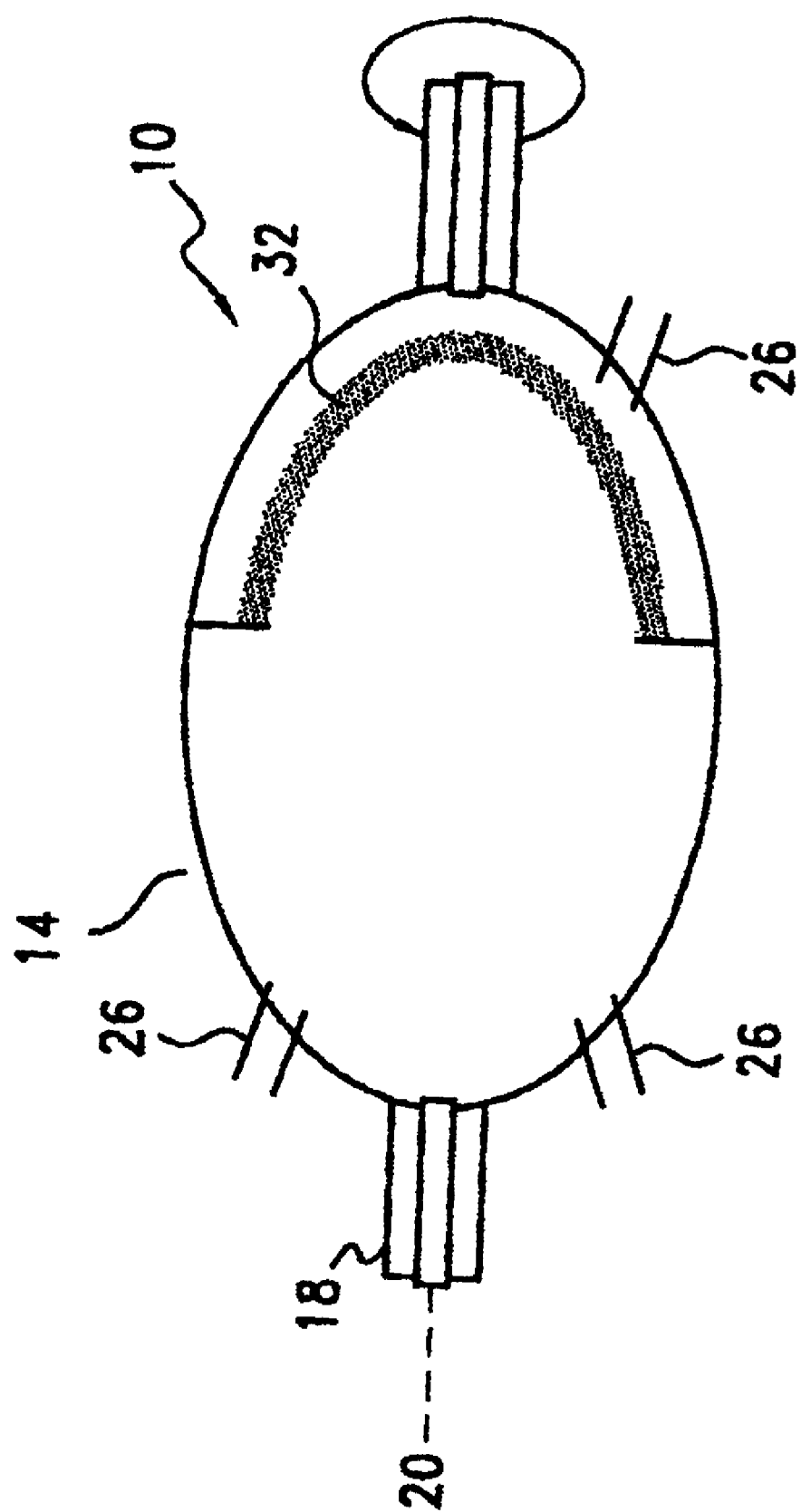
FIG. 3, is a cross sectional view of an ellipsoid culture vessel or bioreactor having a filter portion that surrounds approximately half the cells, cellular aggregates or tissues.

FIG. 3 shows culture vessel or bioreactor 10 having at least one filter 36 disposed in chamber 14 that surround cells, cellular aggregates or tissues. A portion of chamber 14 defined by curved wall 16 is shown having substantially ellipsoid shape. Housing 12 may be rotated about substantially horizontal major axis 20. This ellipsoid shape housing 12 may be used in the system described by FIGS. 1 and 2.

Figure 4:
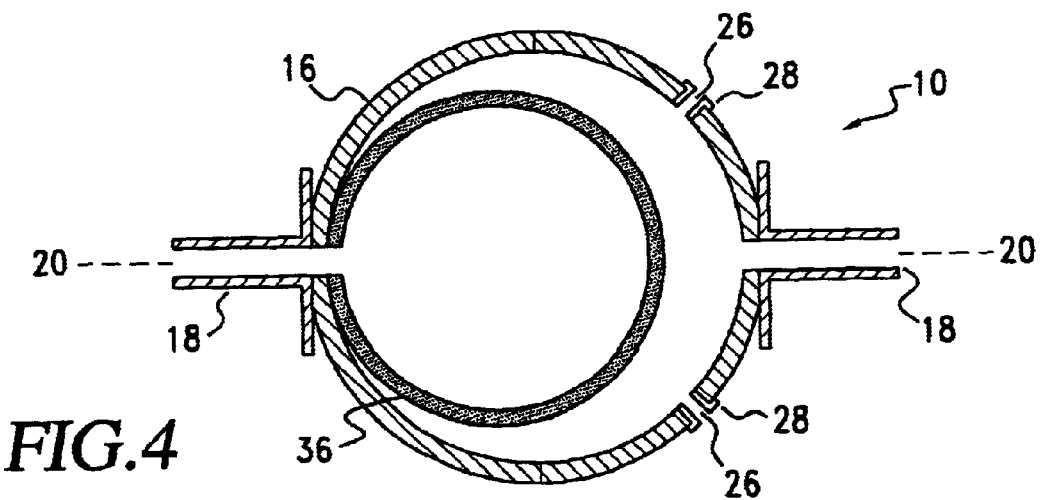
FIG. 4, is a cross sectional view of a culture vessel or bioreactor having a filter disposed about an inlet/outlet port and within a chamber having a substantially spherical shape.

FIG. 4 is a cross sectional view of a culture vessel or bioreactor 10 having a filter 36 disposed about an inlet/outlet port 18 and within a chamber having a substantially spherical shape. Access ports 26 having valves 28 are located on the chamber to provide points to withdraw samples and add cells, tissues or other materials to the culture.

Figure 5:
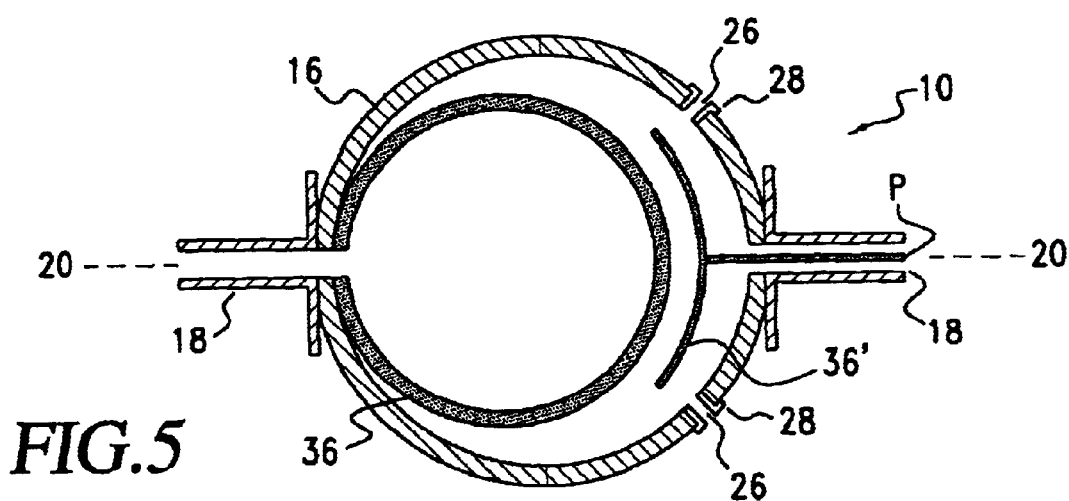
FIG. 5, is a cross sectional view of a culture vessel or bioreactor having at least one filter disposed about an inlet/outlet port and a diffusion plate extending through an inlet/outlet port into the chamber and forming a concave shape. The chamber having a substantially spherical shape.

FIG. 5 is a cross sectional view of a culture vessel or bioreactor 10 having at least one filter 36 disposed about an inlet/outlet port 18 and a diffusion plate 36' extending through an inlet/outlet port 18 into the chamber and forming a concave shape. The diffusion plate 36' is saucer shaped, typically made out of plastic and is used to induce fluid flow around the front area the filter 36 because debris usually forms near the front area of the filter 36. The diffusion plate 36' is attached to a piece of plastic p, usually by silicon rubber. Silicon rubber is also used to attach filters to the interior walls of the vessel. The chamber having a substantially spherical shape. The chamber in another embodiment may have an extended oblate spherical shape.

Figure 6:
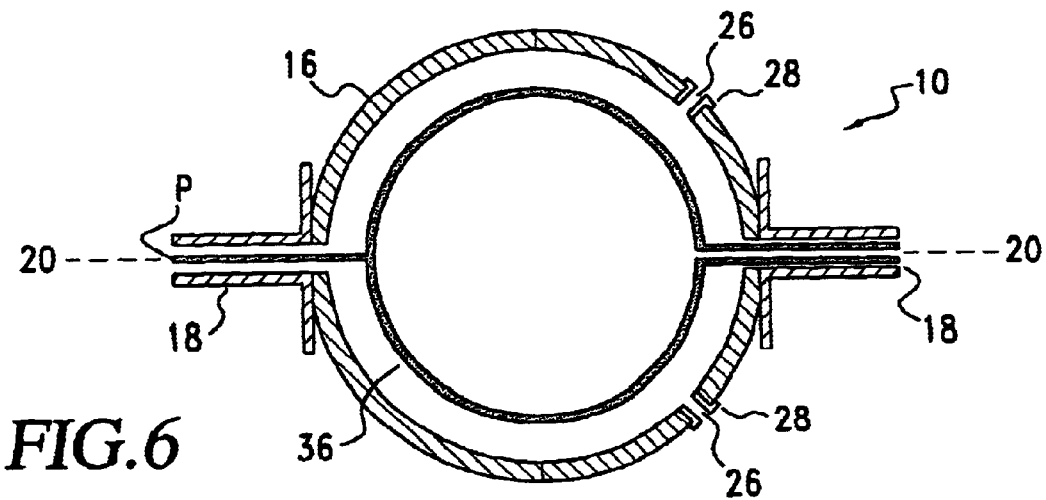
FIG. 6, is a cross sectional view of a culture vessel or bioreactor having a filter that surrounds cells, cellular aggregates or tissues. The chamber having a substantially spherical shape.

FIG. 6 is a cross sectional view of a culture vessel or bioreactor 10 having a filter 36 that surrounds cells, cellular aggregates or tissues. The chamber having a substantially spherical shape. The filter 36 is more centered than the embodiment of FIG. 5.

Figure 7:
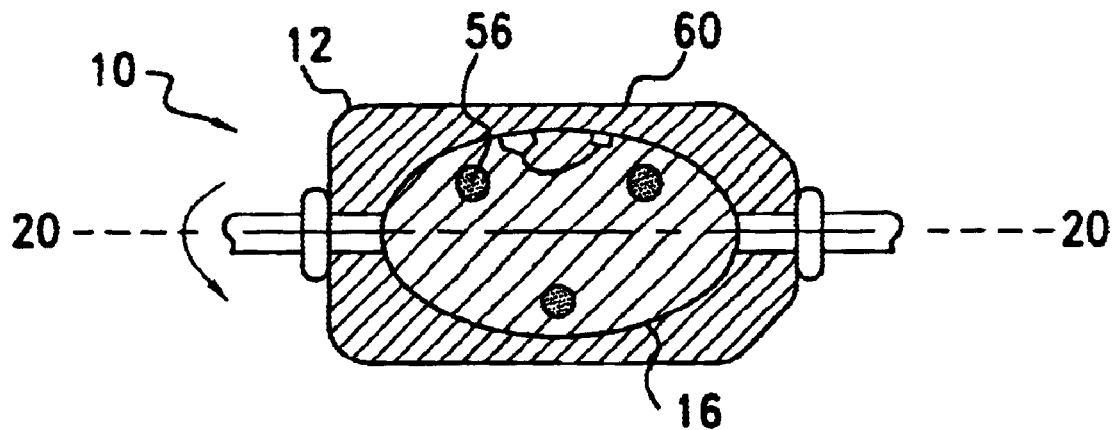
FIG. 7, is a cross sectional view of a culture vessel or bioreactor having a filter disposed about a portion of a chamber having substantially ellipsoid shape with bubble removing means.

FIG. 7 shows culture vessel or bioreactor 10 having at least one filter 56, or preferably a plurality of filters 56, disposed about chamber 14 defined by curved wall 16. Such filter 56 is in fluid communication with culture media being supplied to the vessel. Bubble removing means 60 is shown in fluid communication with chamber 12. Preferably, such means includes a recession structured to trap bubbles and a port in fluid communication with the recession both structured in combination to release the trapped bubbles.

Figure 8:
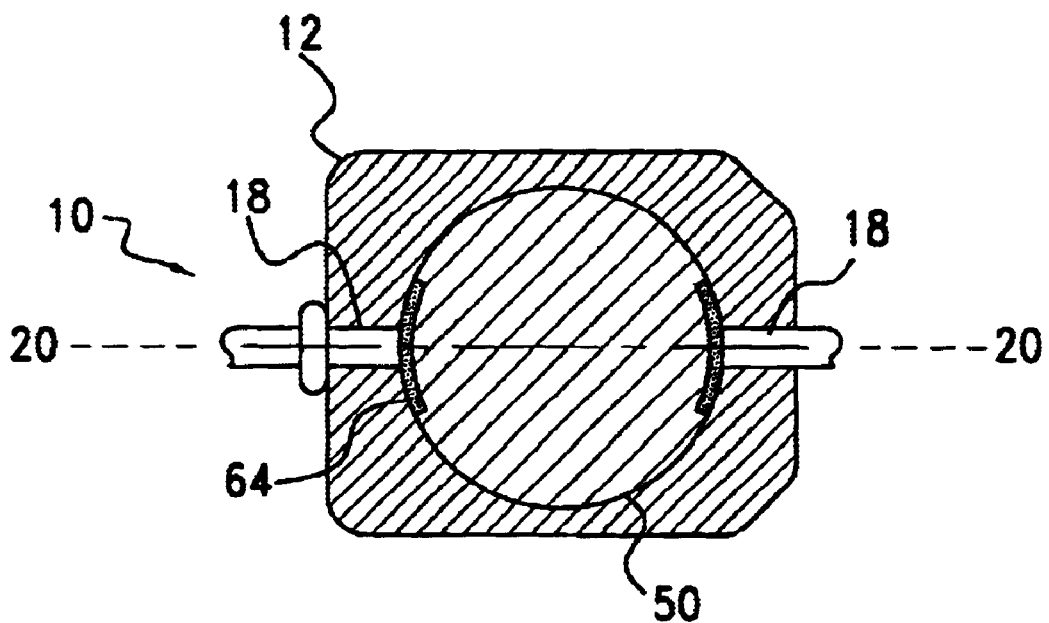
FIG. 8, is a cross sectional view of a culture vessel or bioreactor having at least one filter and bubble removing means disposed about curved chamber walls.

FIG. 8 shows culture vessel or bioreactor 10 having at least one filter 64 in fluid communication with at least one inlet/outlet port 18. A portion of chamber 50 having substantially spherical shape. Housing 12 may be rotated about a substantially horizontal axis 20.

Figure 9:
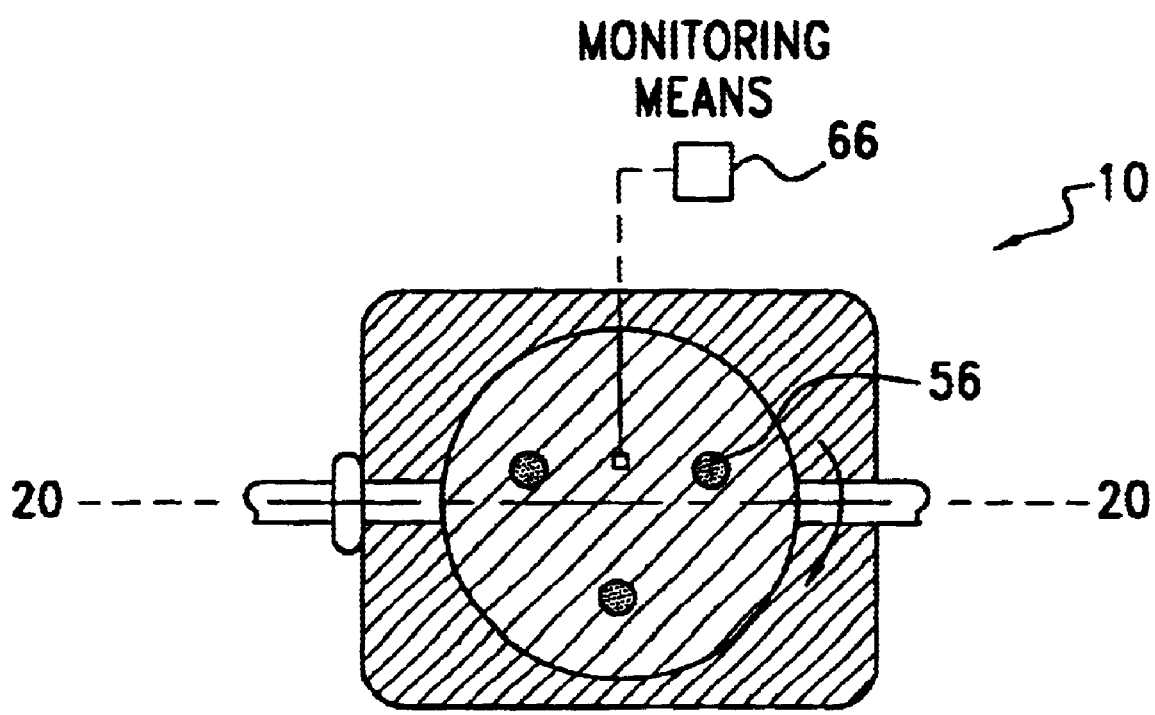
FIG. 9, is a cross sectional view of a culture vessel or bioreactor having at least one filter disposed about an inlet/outlet port of a chamber portion having substantially spherical shape and having monitoring means.

FIG. 9 is an embodiment of the culture vessel or bioreactor 10 is shown as having monitoring means for monitoring the temperature, pressure, glucose, ammonia and PH of the chamber. Also, when vessel 10 is operated in a continuous manner, such as a continuous profuse system, such monitoring means may monitor flow rate of media in and out of said vessel 10. Housing 12 may be rotated about a substantially horizontal axis 20.

Figure 10:
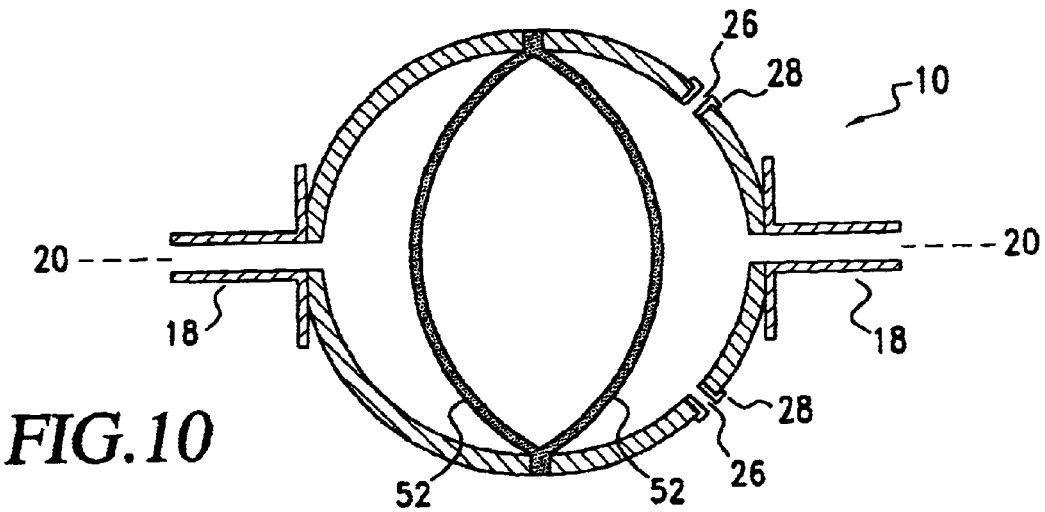
FIG. 10, is a cross sectional view of a culture vessel or bioreactor having a chamber portion of substantially oblate spherical shape. Two filter portions are attached to the walls of the vessel joining together to surround cells, cellular aggregates or tissues.

FIG. 10, is a cross sectional view of a culture vessel 10 or bioreactor having a chamber portion of substantially oblate spherical shape. Two filter portions 52 are attached to the walls of the vessel joining together to surround cells, cellular aggregates or tissues. The filters are typically joined using rubber silicon. Inlet/outlet ports 18 are provided at each end of the vessel, additionally, two access ports 26 and their valves 28 are shown on the vessel 10 body.

Figure 11:
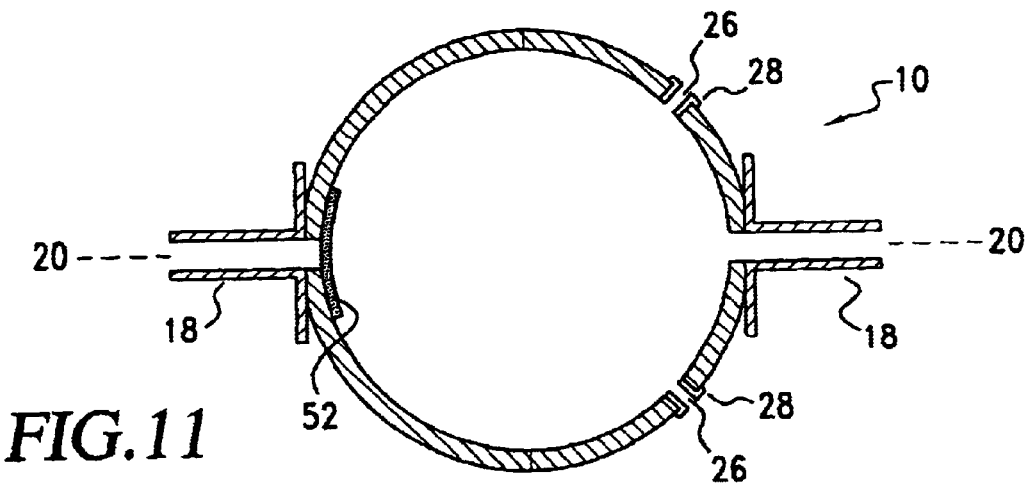
FIG. 11, is a cross sectional view of a culture vessel or bioreactor having a chamber portion of substantially spherical shape. A filter portion is placed flush against an inlet/outlet port.

FIG. 11, is a cross sectional view of a culture vessel 10 or bioreactor having a chamber portion of substantially spherical shape. A filter portion 52 is placed flush against the vessel wall at the inlet/outlet port 18. Flow pathways may be incorporated behind the filter to provide fluid passageways.

Figure 12:
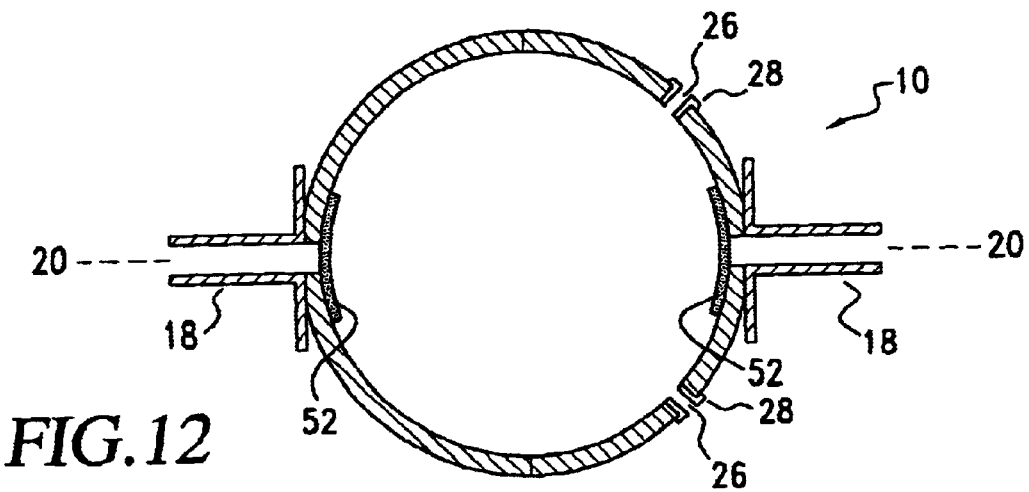
FIG. 12, is a cross sectional view of a culture vessel or bioreactor having a chamber portion of substantially spherical shape having two filter portions, each near an inlet/outlet port.

FIG. 12, is a cross sectional view of a culture vessel 10 or bioreactor having a chamber portion of substantially spherical shape having two filter portions 52, each near an inlet/outlet port 18 on the interior of the vessel. Flow pathways may be incorporated behind the filter to provide fluid passageways.

Figure 13:
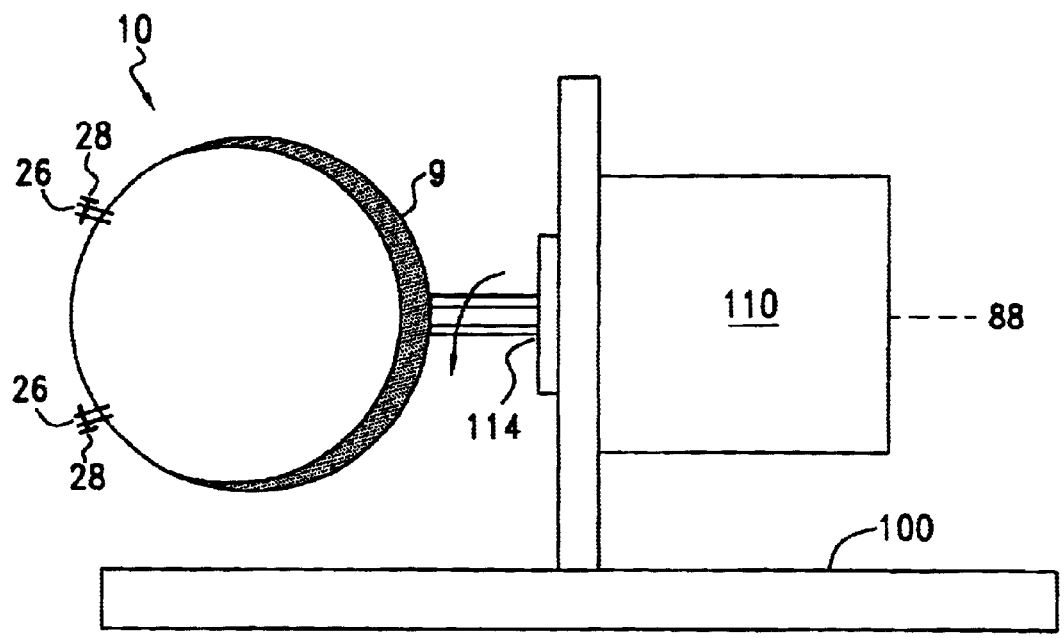
FIG. 13, is a schematic view of a batch culture vessel or bioreactor, substantially spherical shown installed upon a drive motor assembly. A gas permeable membrane is shown.

FIG. 13 shows a batch culture vessel or bioreactor 10 installed on assembly platform 100. Vessel 10 is installed on drive shaft 114 which is connected to drive motor 110. Rotation of drive shaft 114 by drive motor 110 thereby rotates vessel 10 installed thereon. Vessel 10, which is shown rotated around horizontal axis 88, has means 116 for attachment to drive shaft 114. Such means may be a coupling or other suitable fitting. At least part of the batch culture vessel is made of a gas permeable material g.

Figure 14:
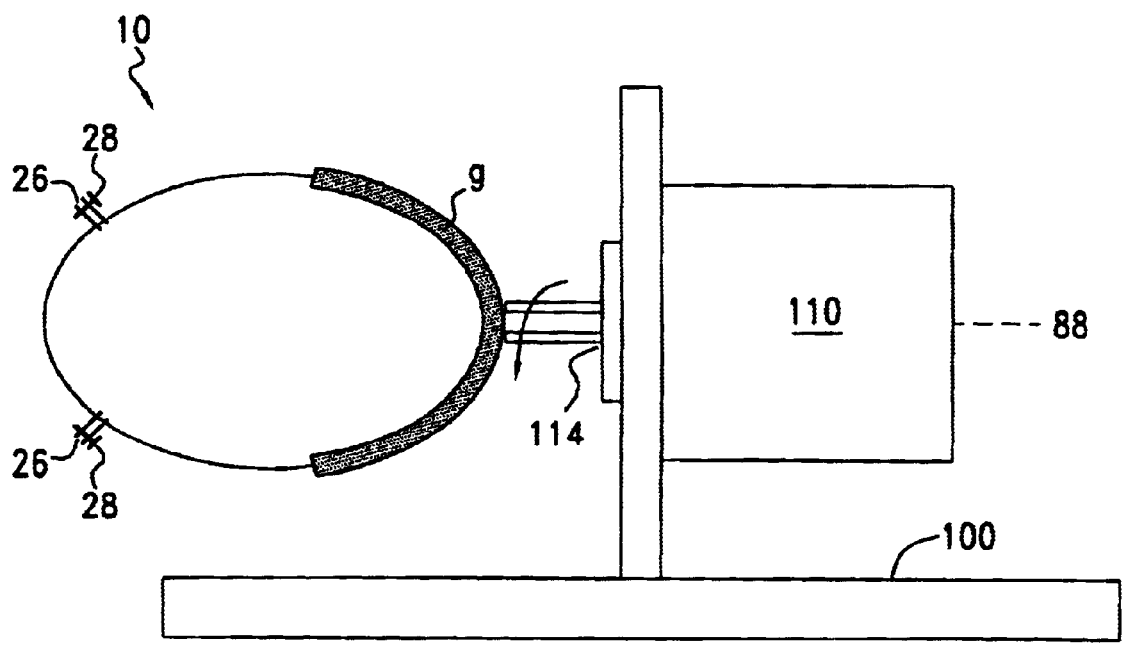
FIG. 14, is a schematic view of a culture vessel or bioreactor, substantially ellipsoid shown installed upon a drive motor assembly. A gas permeable membrane is shown.

FIG. 14 shows a batch culture system that has an ellipsoid shaped culture vessel with a gas permeable wall g. Access ports 26 and valves 28 for opening and closing the ports are disclosed.

Figure 15:
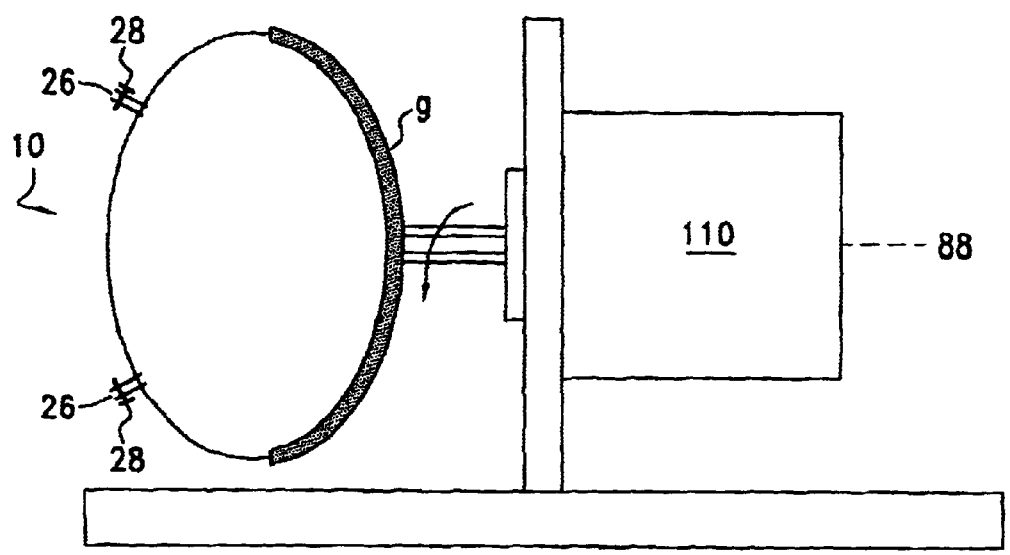
FIG. 15, is a schematic view of a culture vessel or bioreactor, substantially ellipsoid is shown installed upon a drive motor assembly. A gas permeable membrane is shown.

FIG. 15 shows a batch culture system that has an ellipsoid shaped culture vessel with a gas permeable wall g. Access ports 26 and valves 28 for opening and closing the ports are disclosed.

Figure 16:
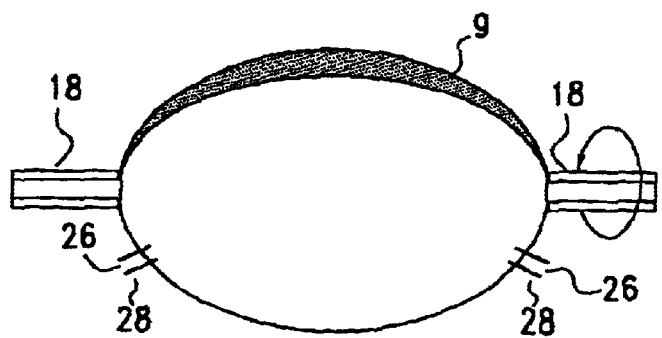
FIG. 16, is a cross-section of a culture vessel or bioreactor, substantially ellipsoid for use in the invention of FIG. 14.

FIG. 16 shows a batch culture system that has an ellipsoid shaped culture vessel with a gas permeable wall g. Access ports 26 and valves 28 for opening and closing the ports are disclosed. This culture vessel is usable in the system disclosed in FIG. 15.

Figure 17:
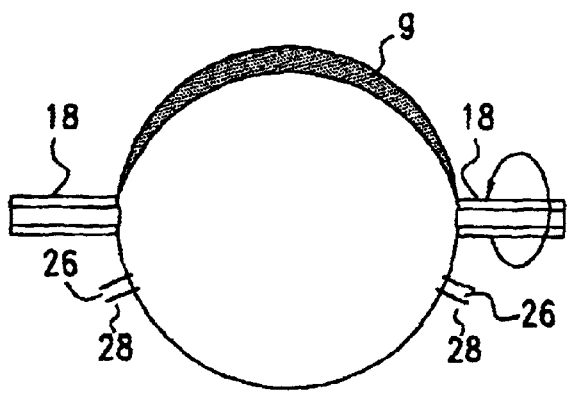
FIG. 17, is a schematic view of a culture vessel or bioreactor, substantially spherical for use in the invention of FIG. 13.

FIG. 17 shows a batch culture system that has an spherical shaped culture vessel with a gas permeable wall g. Access ports 26 and valves 28 for opening and closing the ports are disclosed. This culture vessel is usable in the system disclosed in FIG. 15.

Figure 18:
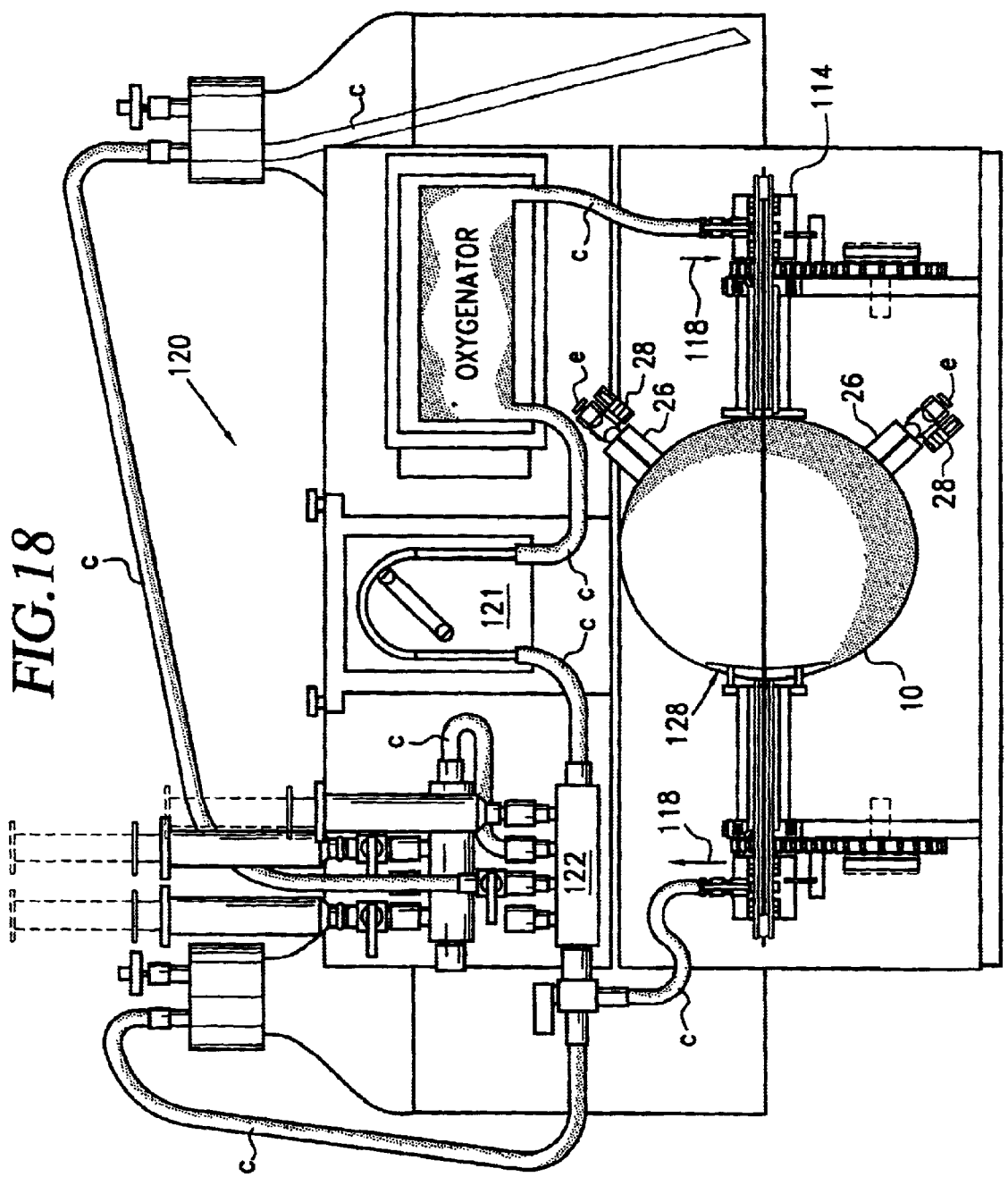
FIG. 18, is a schematic view of a perfused cell culture system with a substantially spherical culture vessel or bioreactor of the present invention.
Figure 19:
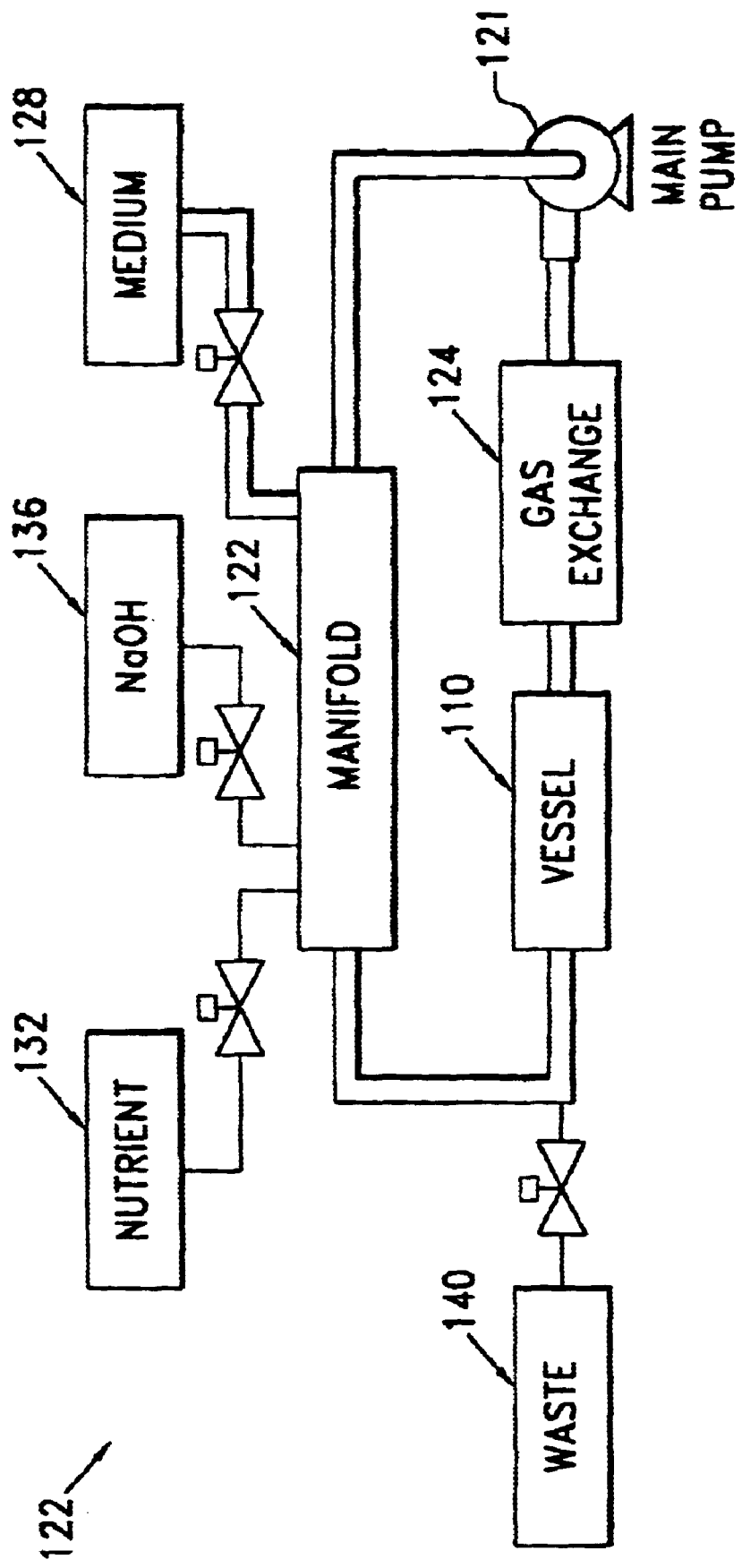
FIG. 19, shows a process flow diagram illustrating manifold means for fluid flow around the culture vessel or bioreactor of the present invention.

FIGS. 18 and 19 shows an assembly 120 of culture vessel or bioreactor 10 along with the attendant devices for operation in a perfused continuous manner. Vessel 10 is installed on drive 114 via coupling 114 and inlet/outlet port 118. Coupling 114 or other means permit vessel 10 to be rotated on shaft 114 and for fluid communication between inlet/outlet port 118 and the conduits C for fluid flow though the assembly. At least one filter 128 is in fluid communication with inlet/outlet port 118. Access port 26 has a valve 28 that allows it to be opened and closed in order to either take a sample or to add materials into the system. Access port 26 has an end cap e which covers the opening when the port is not being accessed. Conduit C connects inlet/outlet port 118 to the suction side of pump 121. The discharge of pump 121 is connected to a manifold means 122 for adding nutrients and culture media and for removing wastes. Means 122 is connected via conduit back to inlet/outlet port 118.

Figure 20:
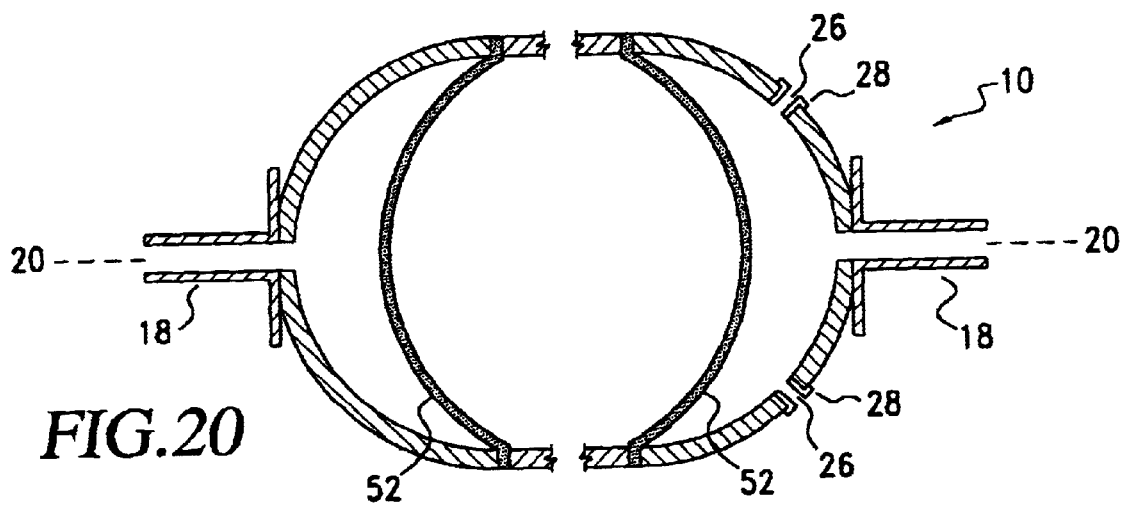
FIG. 20, is a cross sectional view of a culture vessel or bioreactor having a chamber portion of substantially extended oblate spherical shape having two filter portions, each attaching to a wall portion of the vessel.

FIG. 20, is a cross sectional view of a culture vessel 10 or bioreactor having a chamber portion of substantially extended oblate spherical shape having two filter portions 52, each attaching to a wall portion of the vessel, while being spaced from the inlet/outlet 18. The filters work together to surround the cells, cellular aggregates or tissues, and allowing nutrients and dissolved gases to flow into the filter enclosure and waste materials to flow out therefrom. Typically oxygen flows in as a dissolved gas, while carbon dioxide flows out as a dissolved gas.

Figure 21:
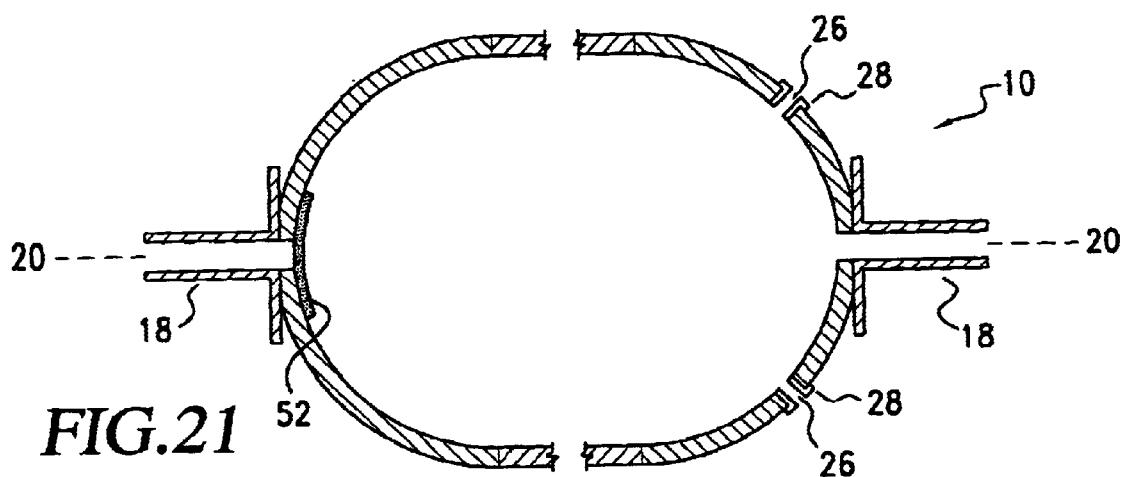
FIG. 21, is a cross sectional view of a culture vessel or bioreactor having a chamber portion of substantially extended oblate spherical shape having one filter portions, each near an inlet/outlet port.

FIG. 21, is a cross sectional view of a culture vessel or bioreactor 10 having a chamber portion of substantially extended oblate spherical shape having one filter portion 52, near an inlet/outlet port 18.

Figure 22:
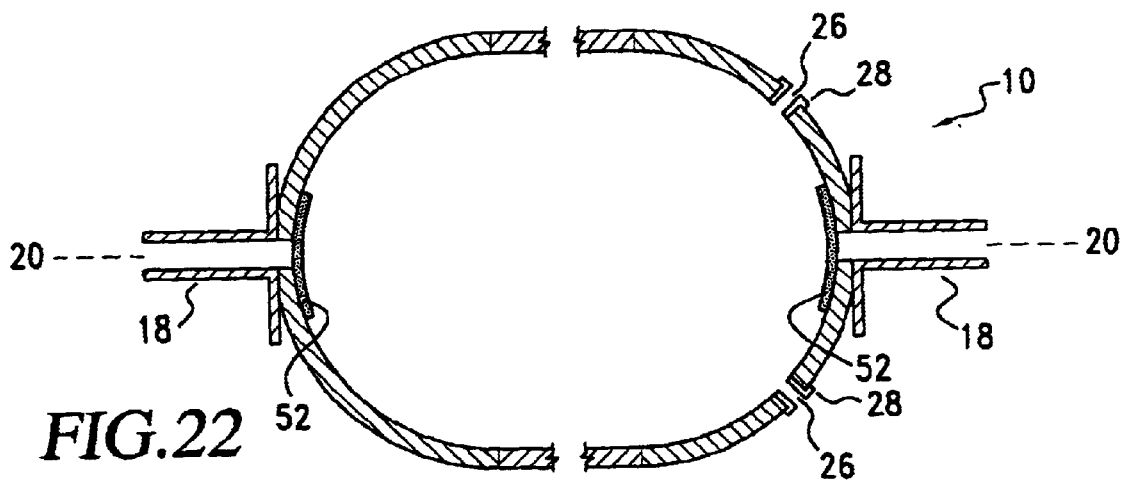
FIG. 22, is a cross sectional view of a culture vessel or bioreactor having a chamber portion of substantially extended oblate spherical shape having two filter portions, each near an inlet/outlet port.

FIG. 22, is a cross sectional view of a culture vessel or bioreactor 10 having a chamber portion of substantially extended oblate spherical shape having two filter portions 52 ,each near an inlet/outlet port 18.

Figure 23:
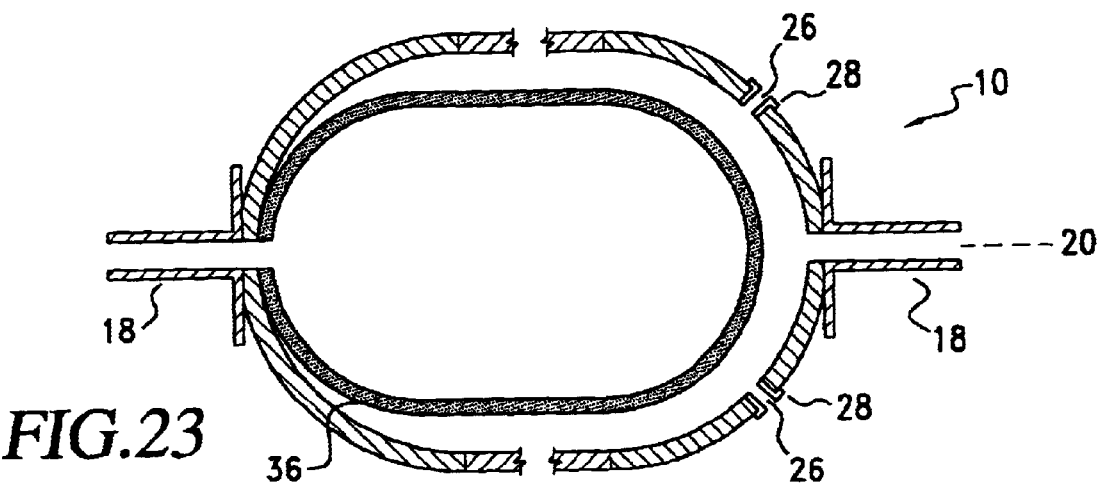
FIG. 23, is a cross sectional view of a culture vessel or bioreactor having a chamber portion of substantially extended oblate spherical shape having one filter portion, that surrounds cells, cellular aggregates or tissues in the chamber portion with an opening near one inlet/outlet port.

FIG. 23, is a cross sectional view of a culture vessel 10 or bioreactor having a chamber portion of substantially extended oblate spherical shape having one filter portion 36, that surrounds cells, cellular aggregates or tissues in the chamber portion with an opening near one inlet/outlet port 18.

Figure 24:
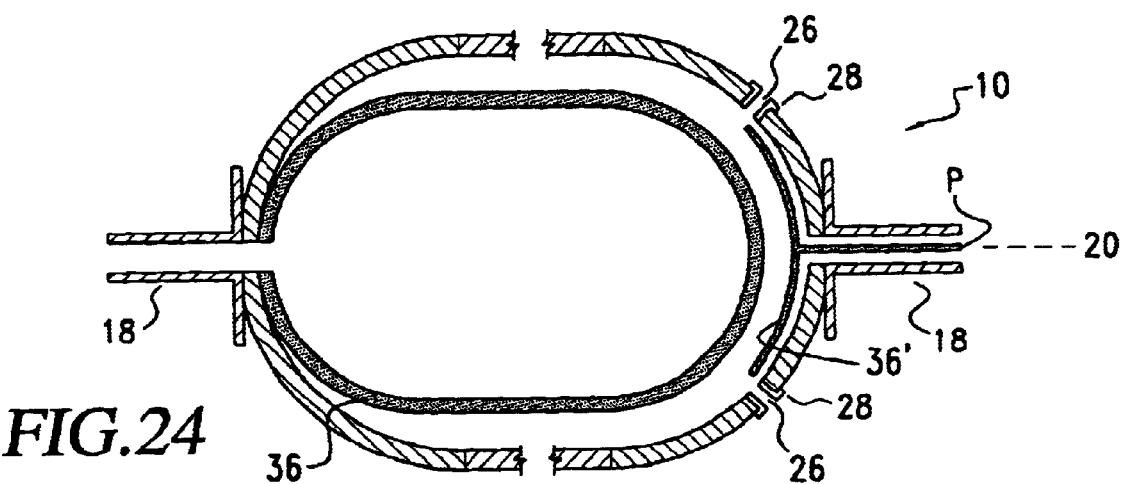
FIG. 24, is a cross sectional view of a culture vessel or bioreactor having a chamber portion of substantially extended oblate spherical shape having one filter portion, that surrounds cells, cellular aggregates or tissues in the chamber portion with an opening near one inlet/outlet port. Another filter extending through an inlet/outlet port into the chamber and forming a concave shape.

FIG. 24, is a cross sectional view of a culture vessel 10 or bioreactor having a chamber portion of substantially extended oblate spherical shape having one filter portion 36, that surrounds cells, cellular aggregates or tissues in the chamber portion with an opening near one inlet/outlet port 18. A diffusion disk 36' is spaced from the filter 36 and surrounds part of the filter by forming a concave shape. The disk has a plastic portion p attached which allows for manual positioning through the inlet/outlet port 18.

Figure 25:
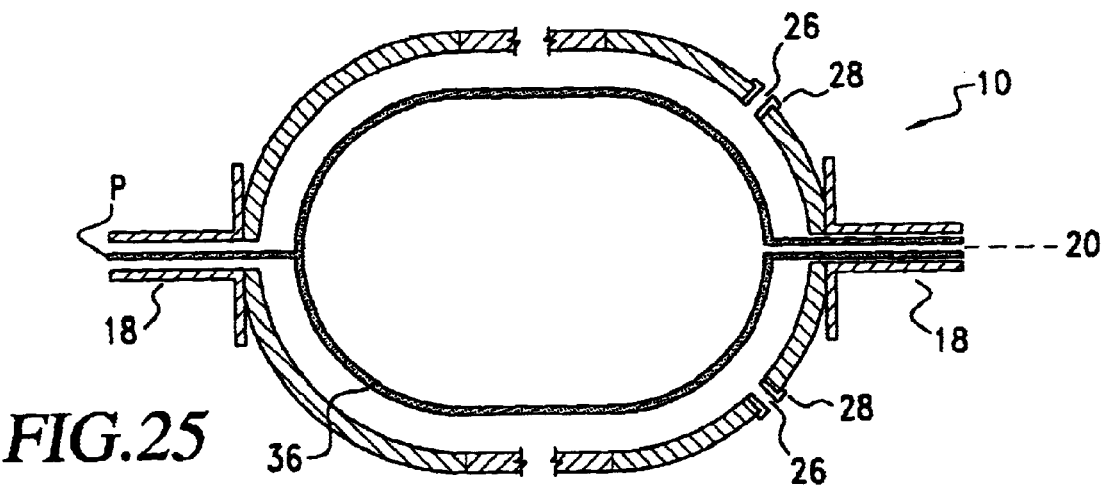
FIG. 25, is a cross sectional view of a culture vessel or bioreactor having a chamber portion of substantially extended oblate spherical shape having one filter portion, that surrounds cells, cellular aggregates or tissues in the chamber portion with an opening near both inlet/outlet ports.

FIG. 25, is a cross sectional view of a culture vessel 10 or bioreactor having a chamber portion of substantially extended oblate spherical shape having one filter portion 36, that surrounds cells, cellular aggregates or tissues in the chamber portion with an opening near both inlet/outlet ports 18.

Figure 26:
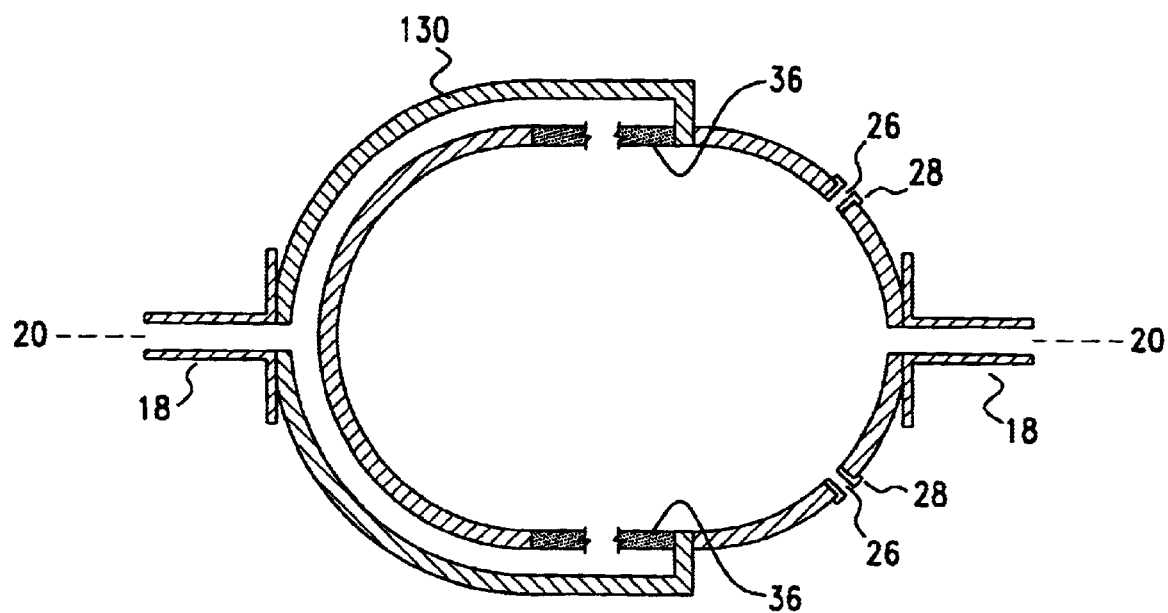
FIG. 26, is a cross sectional view of a culture vessel or bioreactor having a chamber portion of substantially extended oblate spherical shape having filter portions near inlet/outlet ports, or built into the wall structure, an exterior wall surrounds over half the vessel and channels the flow to one port.

FIG. 26, is a cross sectional view of a culture vessel or bioreactor having a chamber portion of substantially extended oblate spherical shape having filter portions 36 integral with the wall structure, an exterior wall 130 surrounds the portion of the vessel that has the filter and channels the flow to one port 18. At least a portion of the vessel wall constructed of gas permeable material 36.

Figure 27:
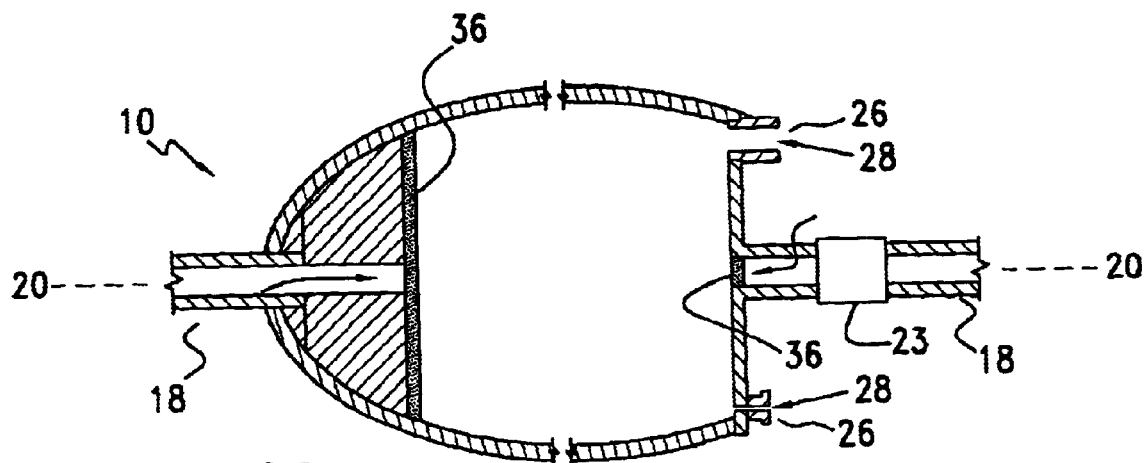
FIG. 27, is a cross sectional view of a culture vessel or bioreactor having a chamber portion of substantially ellipsoid or cylindrical shape having two filter portions, one within the chamber near an inlet/outlet ports, the other within the conduit of the inlet/outlet port. It should be clear that this smaller filter within

FIG. 27, is a cross sectional view of a culture vessel 10 or bioreactor having a chamber portion of substantially cylindrical shape having two filter portions 36, one within the chamber near an inlet/outlet port 18, the other within the conduit of the inlet/outlet port 18. A rotative coupling 23 is used to attach the vessel to the conduit. The vessel is rotated in a substantially horizontal plane 20.

Figure 28:
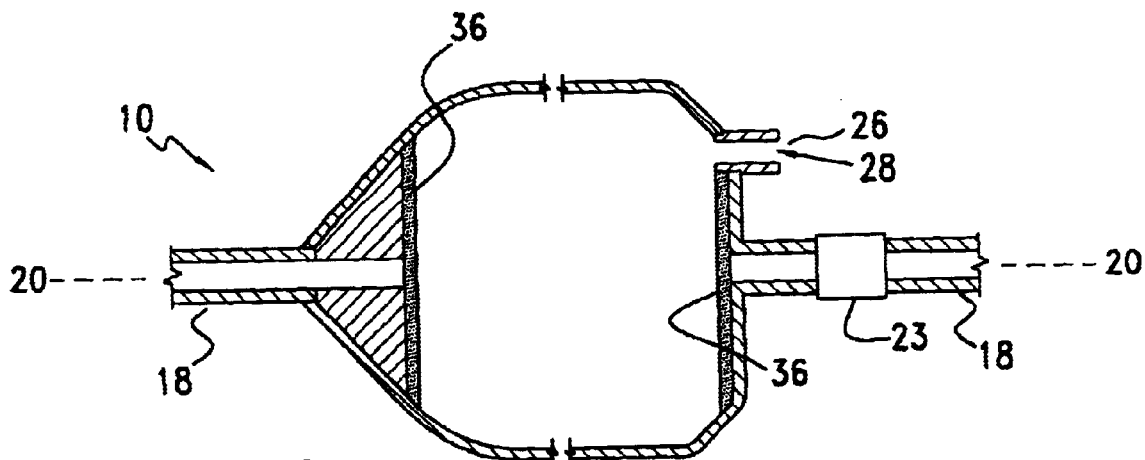
FIG. 28, is a cross sectional view of a culture vessel or bioreactor having a chamber portion of substantially substantially ellipsoid or cylindrical shape having filter portions near inlet/outlet ports.

FIG. 28, is a cross sectional view of a culture vessel 10 or bioreactor having a chamber portion of substantially substantially cylindrical shape having filter portions 36 near inlet/outlet ports 18. A rotative coupling 23 is used to attach the vessel to the conduit. The vessel is rotated in a substantially horizontal plane 20.

Figure 29:
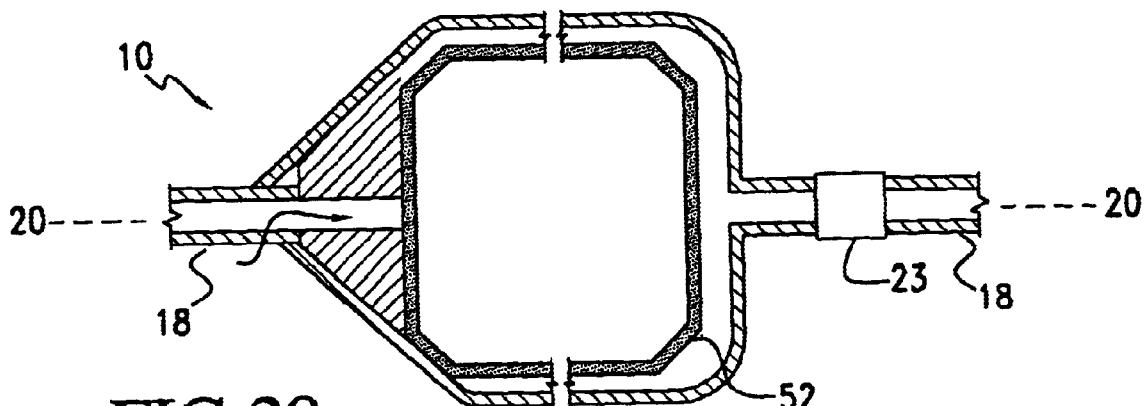
FIG. 29, is a cross sectional view of a culture vessel or bioreactor having a chamber portion of substantially extended oblate cylindrical shape having a filter portion that surrounds cells, cellular aggregates or tissues in the chamber portion.

FIG. 29, is a cross sectional view of a culture vessel 10 or bioreactor having a chamber portion of substantially extended oblate cylindrical shape having a filter portion 52 that surrounds cells, cellular aggregates or tissues in the chamber portion. A rotative coupling 23 is used to attach the vessel to the conduit. The vessel is rotated in a substantially horizontal plane 20.

Figure 30:
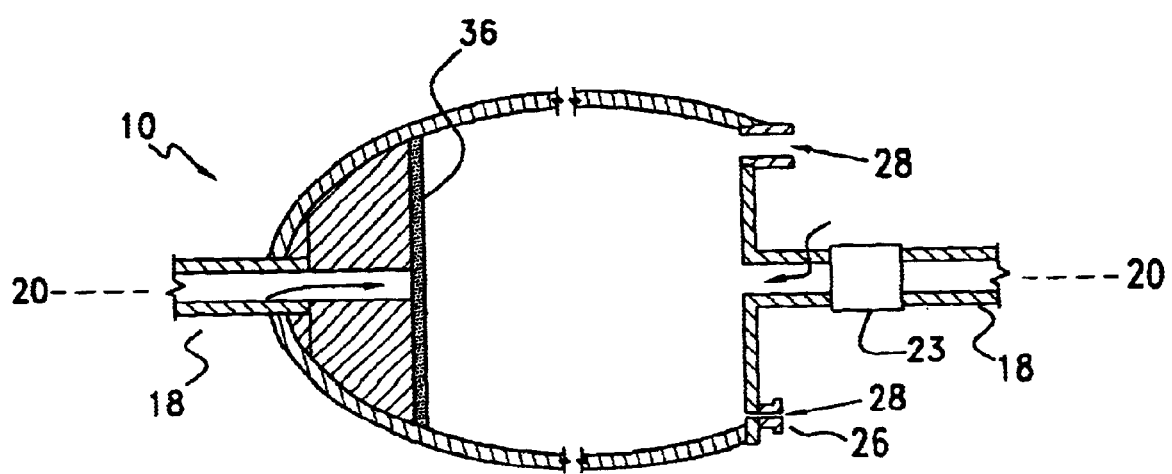
FIG. 30, is a cross sectional view of a culture vessel or bioreactor having a chamber portion of substantially ellipsoid or cylindrical shape having one filter portion, within the chamber near an inlet/outlet ports.

FIG. 30, is a cross sectional view of a culture vessel 10 or bioreactor having a chamber portion of substantially ellipsoid or cylindrical shape having one filter portion 36, within the chamber near an inlet/outlet ports 18. A rotative coupling 23 is used to attach the vessel to the conduit. The vessel is rotated in a substantially horizontal plane.

Referring again to FIGS. 15–18, the preferred means for rotation is a drive motor 110 or a motor assembly (not shown). Such motor assembly should be capable of rotating the culture vessel 10 at a variety of rates of rotation. A motor assembly may be fixed to mounting base and may be provided with attachment means for attaching to and rotating vessel 10. Attachment means may comprise threadably connecting screw threads 116 on vessel 10 to corresponding threads on the motor assembly. Such screw threads maybe in a direction so that inadvertent loosening of the vessel 10 from the motor assembly will avoid rotational wobbling. In addition, a lock nut or similar device may be provided on drive shaft 114 to prevent loosening or further wobbling. It is preferred, however, that attachment means be a serpentine or KEVLAR® belt or belts that cause drive shaft 114 and vessel to be fixedly attached together and to rotate about a substantially horizontal axis.

Another means for rotation is a roller mechanism having multiple rollers arranged longitudinally in a substantially horizontal plane. Such roller mechanism should be capable of rotating the culture vessel 10 at a variety of rates of rotation. The rollers are rotated simultaneously to rotate a culture vessel laid between the rollers. Such roller mechanism may be obtained from Stoval Life Science Inc., however, other roller mechanisms that will provide controlled rotation may also be used.

Culture vessel 10 may be rotated at a variety of rotation rates. A preferred rotational rate or speed is in the range of about 2.0 revolutions per minute (rpm) to about 45 rpm. The desired rotational rate or speed is a function of the specific dimensions of vessel 10 and the sedimentation rates of the cells and tissue particles or organoids for a given application. The sedimentation rate is visually determined by an experienced operator. The rotation rate for a typical organoid type of culture (for example, liver tissue) may be in the range of 18–24 rpm. The rotation rate for suspension cells (for example, lymphocytes) and other cells that tend to remain individual cells and do not adhere is between 8–10 rpm. ATCC, Inc. of Atlanta, Ga. is one source for an established suspension cell line. Also, it is expected that the rotational rate or speed should be adjusted to balance the gravitational forces in order to maximize free expansion of non-linear toroidal flow of the growing cells, cellular aggregates or tissues. Further, it is expected that as the density and/or size of cells, cellular aggregates or tissues, increases the rotational rate or speed of vessel 10 may be increased as needed to maintain non-linear toroidal flow.

FIG. 18 shows a detail of the attendant devices of manifold means 122. Manifold 142 of manifold means 122 is in fluid communication with at least one of a source of culture media 128, a PH adjustment source 136 (preferably NaOH), a nutrient source 132, and a waste storage apparatus 140. Also, manifold 142 is in fluid communication with culture vessel 110, gas exchange device 124 and pump 121.

Gas exchange device 124, also in fluid communication with pump 121, may be characterized as an oxygenator, but the device should be capable of maintaining desired gas concentrations for the variety of gases needed to sustain and promote cellular respiration. Oxygen is consumed and carbon dioxide is produced by the growing cells, cellular aggregates or tissues in the culture chamber. As a result, gas exchange device 124 must be capable transferring oxygen into the media and removing carbon dioxide from the media. If oxygen and carbon dioxide is not properly balanced and/or controlled, the increasing concentration of carbon dioxide will inhibit the growth of, or kill the culture. Lactic acid would also kill the culture. If acidic PH in the circulating culture media is encountered, then a compound from PH adjustment source 136 may be added to adjust PH to more neutral PH levels.

Pump 121 may be used to maintain culture media flow though vessel 110. Preferably, pump 121 is peristaltic pump or similar device that is capable of maintaining a relatively constant culture media flow through the vessel and through the attendant devices for operation in a continuous manner, discussed above. Pump 121 may be operated and/or adjusted to a variety of flow rates and is capable of reversing the direction of medium flow thorough the vessel and attendant devices.

In any one of the embodiments of this invention, housing 12 may be structured of any suitable material. In a preferred batch culture embodiment, at least part of housing 12 may be structured to be gas permeable so that atmospheric gases, such as oxygen and carbon dioxide may permeate the housing and assist in respiration of growing cells, cellular aggregates or tissues. The gas permeable member that is within the vessel is typically made of a silicon rubber compound or TEFLON®. Other alternative materials for a gas permeable membrane are foam plastic or radiation treated plastic. One factor that reduces the effectiveness of the gas permeable membrane g is the build up over a period of time of mucin.

Under continuous operating condition, cells, cellular aggregates or tissues may be introduced in culture media to form a mixture. Preferably, such mixture may be added directly to vessel chamber 14 through an access port 26. The access port may be a fill port, sample port or a septum. A valve may be placed in the access port and have an open and a closed position. The way in which fluid from the system may be sampled is by opening the valve manually, inserting a syringe into either the septum or sampling port and withdrawing a given quantity. Likewise, materials may be injected into the vessel. The valve would be turned to a closed position after a sample was withdrawn or materials inserted into the vessel. Typically end caps e are placed over the access port when not in use in order to prevent contaminants from entering the system. Culture media will flow continuously through inlet/outlet port 18 and through filter 22, providing oxygen and nutrients to cells for respiration and growth. Further, cellular materials and waste are removed along with the flowing culture media. Chamber 14 may have a continuous curved wall 16 symmetrical about an axis, an inlet and an outlet. Vessel 10 may have at least one filter in fluid communication with inlet/outlet ports 18 and structured to pass culture media and cellular waste and to retain cells, cellular aggregates or tissues. This mixture is mixed, by rotating the vessel. As this mixture is mixed, the cells, cellular aggregates or tissues are allowed to freely expand in a non-linear toroidal flow path. Culture media growth condition for cells, cellular aggregates or tissues in chamber 14 of vessel may be monitored. The conditions monitored may include the temperature, oxygen, carbon dioxide, PH, ammonia, glucose and other parameters as well as culture media flow rate. Typically, sensors are used to take measurements. A blood gas analyzer could also be utilized.

As cells, cellular aggregates or tissues grow there will be need to replenish nutrients and to exchange oxygen and other gases in the media. Manifold means 122 may be operated to selectively add nutrients from nutrient source 132 to manifold 142. Such nutrients may be mixed with culture media from media source 128 and pumped into culture vessel 10 via pump 121. Wastes may be removed from the vessel by flowing the contents from the vessel through a filter 22. PH of the media may be adjusted by adding a compound from PH adjustment source 136.

Another embodiment of the invention is a method for growing cells, cellular aggregates or tissues. The method includes introducing cells, cellular aggregates or tissues into a culture media mixture in a vessel chamber having a continuous spherical, oblate, oblate spherical, extended spherical, extended oblate spherical or curved wall symmetrical about an axis The cells, cellular aggregates or tissues are mixed, by rotating the vessel about its horizontal axis. The method may further include flowing culture media through the inlet, or reversing flow through the outlet in a continuous manner.

In the batch culture version at least part of the surface of the vessel is made up of gas permeable material so that the cells, cellular aggregates, "organoids" or tissue materials are provided dissolved oxygen and the metabolic dissolved carbon dioxide is removed from the culture vessel. Expended media is removed from the batch culture vessels by stopping the vessel, withdrawing a given amount of expended media and replacing it with fresh media.

Another embodiment of this invention is a method for producing enzymes, hormones or other biological materials in a fluid using cellular mechanisms. The method includes growing or maintaining live cells, tissues or organoids in a culture media. Fluid containing nutrients and oxygen is flowed through the culture of live organoids. Such organoids include liver, pancreatic or glandular organoids as well as other tissues and/or cells that utilize cellular mechanisms to produce enzymes, hormones or other biological products. The cellular mechanism utilized by these organoids are the same as, or are similar to, the mechanisms used by human organs to produce enzymes, hormones and other biological materials in the human body. The mixture is added to a first vessel having a chamber defined by a curved wall symmetrical about an axis, an inlet and an outlet. Oxygen and nutrients are provided to the organoids. The organoids are mixed, by rotating the vessel about its horizontal axis. As the fluid is mixed with the organoids, enzymes, hormones and other biological products are synthesized in the fluid by their cellular mechanisms.

Still another embodiment of this invention is a method for removing biological waste materials from a fluid using cellular mechanisms. The method includes growing or maintaining live cells, tissues or organoids in a culture media. Fluid containing toxins or biological waste material is flowed through the culture of live organoids. Such organoids include liver, kidney, pancreatic organoids as well as other tissues and/or cells that utilize cellular mechanisms to remove waste materials from a fluid. The cellular mechanism utilized by these organoids are the same as, or are similar to, the mechanisms used by human organs to remove toxins and other waste materials from the human body. The mixture is added to a first vessel having a chamber defined by a curved wall symmetrical about an axis, an inlet and an outlet. Oxygen and nutrients are provided to the organoids. The organoids are mixed, by rotating the vessel about its horizontal axis. As the fluid containing waste is mixed with the organoids, waste materials are filtered or metabolized from the fluid by their cellular mechanisms. The waste materials are removed from the fluid using the cellular mechanisms of the organoids.

There is a limit to the quantity of materials that may be removed from the waste containing fluid that may processed through a single vessel 10. As the ability of the suspended organoids to filter wastes and toxins becomes exhausted, the organoids will frequently expire or cease to operate. Therefore, it is preferable for the culture vessel or bioreactor of this invention to have a first vessel in fluid communication with at least one additional vessel. Such vessels are preferably arranged in series. That is, fluid containing waste flowing from a first vessel for a first removal of wastes and then flowing into a second vessel for addition waste removal. This fluid communication between vessels in series allows for more efficient filtering and metabolic processing. Further, this arrangement allows the filtering process to continue without significant interruption when the organoids in a vessel are depleted and must be removed to be replaced with a vessel containing fresh organoids. It is important to note that plastic material is typically used to form the vessel components and that the components are typically ultrasonically welded together. Another alternative to ultrasonic welding is a snap ring with fingers that mate with a corresponding clip portion on the other portion to complete the vessel structure. Other methods of assembly known in the art may be used.

It should be clear that the figures show alternative preferred embodiments of culture vessel or bioreactor 10 of the present invention. These vessels with different shapes and filter/gas permeable membrane or wall arrangements are capable of being rotated at different speed and in use in a perfused system or a batch culture system, as the need may be.

The foregoing description of preferred embodiments of the invention has been presented for purposes of illustration and description, and is not intended to be exhaustive or to limit the scope of the invention to the precise form disclosed. The description was selected to best explain the principles of the invention and their practical application to enable others skilled in the art to make and best utilize the invention. Various other embodiments and modifications may be suited to the particular use contemplated. It is intended that the scope of the invention not be limited by the specification, but be defined by the claims set forth below.

What is claimed is:

1. A culture vessel comprising:
   a housing defining a chamber having at least one inlet and at least one outlet, the housing adapted to rotate about a longitudinal substantially horizontal axis;
   at least one filter within the chamber in fluid communication with an outlet, the filter having openings of a size that allows the passage of a fluid culture medium and cellular metabolic waste but prevents the passage of cells and cellular aggregates;
   the chamber having a substantially unobstructed horizontal axis; and
   a pump in fluid communication with at least one of an inlet or an outlet,
   wherein the chamber is symmetrical about an axis.

2. A culture vessel comprising:
   a housing defining a chamber having at least one inlet and at least one outlet, the housing adapted to rotate about a longitudinal axis;
   at least one filter in fluid communication with an outlet, the filter having openings of a size that allows the passage of a fluid culture medium and a cellular metabolic waste but prevents the passage of cells and cellular aggregates;
   the chamber, in cross-section through a longitudinal axis, having wall portions spherical, oblate spherical, extended spherical or extended oblate spherical wall portions; and a pump in fluid communication with at least one of an inlet or outlet.

3. The culture vessel of claim 1 or 2 wherein one of the at least one inlet, at least one outlet and at least one filter is proximate to the axis.

4. The culture vessel of claim 2 wherein the chamber is symmetrical about an axis.

5. The culture vessel of claim 1 or 2 wherein at least one access port means for accessing culture is located on an exterior surface of the housing.

6. The culture vessel of claim 5 wherein the at least one access port is a sample port with a valve for controlling flow out of the culture.

7. The culture vessel of claim 5 wherein the at least one access port is a septum with an opening for controlling flow out of the culture.

8. The culture vessel of claim 2 wherein at least a portion of the at least one filter is disposed about the wall portion.

9. The culture vessel of claim 1 or 2 wherein the at least one filter substantially surrounds the cells, cellular aggregates or tissues within the chamber.

10. The culture vessel of claim 1 or 2 that includes a valve in fluid communication with the inlet and a culture media source, the valve structure to permit media flow from the media source to the chamber and resist flow from the chamber to the media source.

11. The culture vessel of claim 1 or 2 wherein the longitudinal axis is substantially horizontal.

12. The culture vessel of claim 1 or 2 wherein at least one filter is fabricated from cloth, metal, plastic or other filter material.

13. The culture vessel of claim 2 that includes a cylindrical shaped member, disposed between the spherical, oblate spherical, extended spherical or extended oblate spherical wall portions.

14. The culture vessel of claim 1 wherein the rotation axis of the vessel is substantially horizontal.

15. The culture vessel of claim 1 wherein at least a portion of the chamber has a substantially ellipsoid, oblate ellipsoid, spherical or oblate spherical or extended spherical shape.

16. The culture vessel of claim 1 wherein the vessel volume is increased by an insertion of a cylindrical section between the ellipsoid, oblate ellipsoid, spherical or oblate spherical or extended spherical ends of the vessel.

17. A culture vessel comprising:
   a housing defining a chamber having at least one access port located on the housing;

a gas permeable membrane located within the housing, the gas permeable membrane allowing for the transfer of gases between the chamber and a space outside of the chamber;

the chamber, in cross-section through a longitudinal horizontal axis, having wall portions spherical, oblate spherical, extended spherical or extended oblate spherical wall portions; and means for rotation about the horizontal axis.

18. The culture vessel of claim 17 wherein end caps are sealingly fixed on the at least one access port when not in use.

19. The culture vessel of claim 17 wherein the at least one access port comprises a fill port for allowing culture media to enter or exit the chamber and a sample port means for controlling fluid flow in and out of the culture.

20. The culture vessel of claim 17 wherein at least part of a vessel wall is gas permeable.

21. The culture vessel of claim 1 or 17 wherein the housing includes means for removing bubbles from the culture media, the means in fluid communication with the chamber.

22. The culture vessel of claims 1, 2 or 17 wherein the bubble removing means includes a recession and a port, the recession in fluid communication with the chamber and structured to trap bubbles, the port in fluid communication with the recession and structured to release the trapped bubbles.

23. The culture vessel of claims 1, 2 or 17 wherein the housing includes means for accessing the fluid in the chamber.

24. The culture vessel of claim 1 wherein at least one chamber includes means for monitoring temperature, oxygen, carbon dioxide and PH.

25. The culture vessel of claims 1, 2 or 17 is constructed to be disposable.

26. The culture vessel of claims 1, 2 or 17 that is constructed to be reusable.

27. The culture vessel of claim 1 or 2 wherein at least one chamber includes means for monitoring culture media flow rate.

28. The culture vessel of claim 1 or 2 further comprising a gas exchange device in fluid communication with the pump, the gas exchange device exchanging gases into and out of the culture media.

29. The culture vessel of claim 1 or 2 wherein the direction of the flow of the media into and out of the vessel can be reversed.

30. The culture vessel of claim 1 or 2 wherein the pump is structured to flow culture media from the inlet to the outlet or from the outlet to the inlet.

31. The culture vessel of claim 1 or 2 wherein the pump is structured to operate at one or more flow rates.

32. The culture vessel of claims 1, 2 or 17 wherein the rotating means is structured to rotate the housing at one or more rotation rates.

33. A method for growing cells, cellular aggregates or tissues in a rotatable culture vessel, comprising the steps of:

filling a rotatable culture vessel having a culture chamber with an unobstructed longitudinal axis with fluid culture media, wherein the culture chamber is symmetrical about an axis;

introducing cells, cellular aggregates and/or tissues into the media;

maintaining media flow through the vessel to provide oxygen and materials to the growing cells and to remove cellular metabolic wastes; and rotating the vessel to suspend the growing cells in the media.

34. A method for growing cells, cellular aggregates or tissues in a rotatable culture vessel, comprising the steps of:

providing a gas permeable membrane for providing oxygen to a culture chamber and removing carbon dioxide and;

filling a rotatable culture vessel having the culture chamber with an unobstructed longitudinal horizontal axis with fluid culture media, wherein the culture chamber is symmetrical about an axis;

introducing cells, cellular aggregates and/or tissues into the media and;

rotating the vessel to suspend the growing cells in the media.

35. The method of claim 33 further comprising continuously or intermittently flowing culture media through the inlet, the outlet or the filter.

36. The method of claim 33 wherein the flowing step includes flowing culture media to provide oxygen and nutrients to cells, cellular aggregates, or tissues and to remove cellular materials and waste.

37. The method of claim 33 or 34 wherein the cells, cellular aggregates or tissues are suspended in the fluid culture medium by rotating the vessel about its horizontal or proximate horizontal axis.

38. The method of claim 37 wherein the rotation rate is varied.

39. The method of claim 37 wherein the rotation step includes allowing the cells, cellular aggregates or tissues to move, traverse or expand in a three-dimensional, random, toroidal path.

40. The method of claim 33 or 34 further comprising the step of monitoring culture media parameters: temperature, oxygen, carbon dioxide, and PH levels.

41. The method of claim 33 or 35 further comprising monitoring the flow rate of the flowing culture media.

42. A method for using cellular mechanisms to secrete biological products in the media or to remove biological waste materials or toxins from the media, comprising the steps of:

filling a rotatable culture vessel having a culture chamber with an unobstructed longitudinal axis with fluid culture media;

introducing cells, cellular aggregates, or tissues into the media to form a mixture;

providing oxygen and nutrients to the cells, cellular aggregates, or tissues; and secreting biological products or removing waste materials using cellular mechanisms.

43. A method for using cellular mechanisms to secrete biological products into the media or to remove biological waste materials or toxins from the media, comprising the steps of:

introducing culture media into a culture vessel chamber having a spherical, oblate spherical, an extended spherical, or continuous curved wall symmetrical about an axis, an inlet and an outlet, the chamber having at least one filter in fluid communication with the inlet or outlet, the filter structured to pass culture media and to retain cells, cellular aggregates or tissues;

introducing cells, cellular aggregates, or tissues into the media to form a mixture;

rotating the culture chamber vessel about the horizontal or proximate horizontal axis;

providing oxygen and nutrients to the cells, cellular aggregates, or tissues; and secreting biological products, or removing waste materials using cellular mechanisms of the cells, cellular aggregates, or tissues.

44. A method for using cellular mechanisms to secrete biological products into the media or to remove biological waste materials or toxins from the media, comprising the steps of:

providing a gas permeable membrane within a culture vessel chamber, the gas permeable membrane allowing for the transfer of gases between the chamber and a space outside of the chamber;

introducing culture media into the culture vessel chamber having a spherical, oblate spherical, an extended spherical, or continuous curved wall symmetrical about an axis, an inlet and an outlet, introducing cells, cellular aggregates, or tissues into the culture media in the vessel to form a mixture;

rotating the culture chamber vessel about the horizontal or proximate horizontal axis;

providing oxygen and nutrients to the cells, cellular aggregates, or tissues; and secreting biological products, or removing waste materials using cellular mechanisms of the cells, cellular aggregates, or tissues; and providing at least one access port for inserting or removing material from the vessel.

45. The method of claim 42 wherein cells, cellular aggregates, or tissues are suspended by rotating the vessel about its horizontal or essentially horizontal axis.

46. The method of claim 42 further comprising the step of flowing the mixture from the first vessel to at least one additional vessel in fluid communication with the first vessel wherein the vessels are arranged in series.

47. The method of claim 46 further comprising the step of periodically removing a vessel containing depleted cells, cellular aggregates, or tissues from the series and adding a vessel containing fresh cells, cellular aggregates, or tissues to the series.

48. A culture vessel comprising:

a cylindrical vessel having first and second end walls and a cylindrical wall therebetween, at least one inlet, at least one outlet, and at least one filter, the at least one filter having openings of a size that allows the passage of a fluid culture medium and cellular metabolic waste but prevents the passage of cells and cellular aggregates;

a growth chamber defined by the cylindrical wall, the fist and second end walls, and the at least one filter, the growth chamber having an unobstructed horizontal axis, wherein the growth chamber is symmetrical about an axis;

means for rotating the tubular vessel about a substantially horizontal longitudinal axis, said rotation means capable of rotating the vessel at a variety of speeds; and a pump for maintaining a flow of fluid culture medium through the growth chamber, the pump capable of maintaining a variety of flow rates and reversing the direction of flow.

49. The culture vessel of claim 48, further comprising at least one access port on at least one of an end wall or cylindrical wall thereby providing access to the growth chamber.

50. The culture vessel of claim 48, further comprising means for removing bubbles from the growth chamber.

51. The culture vessel of claim 48, wherein the outlet is located on the second end wall.

52. The culture vessel of claim 48, wherein the at least one filter is attached to the cylindrical wall and spaced apart from the first end wall.

53. The culture vessel of claim 48, wherein the at least one filter is connected to the inlet and the first end wall.

54. The culture vessel of claim 48, wherein said at least one filter comprises a first filter and a second filter, wherein the first filter is connected to the inlet and the first end wall.

55. The culture vessel of claim 54, wherein the second filter is attached to the cylindrical wall and spaced apart from the second end wall.

56. The culture vessel of claim 54, wherein the second filter is connected to the outlet and to the second end wall.

57. The culture vessel of claim 48, wherein there is a plurality of outlets located about the periphery of at least one of the second end wall or cylindrical wall that are in fluid communication with a centralized outlet.

58. The culture vessel of claim 54, wherein the first filter is cylindrical in shape and is adjacent to and spaced apart from the cylindrical wall.

59. The culture vessel of claim 54, wherein the first filter is cylindrical in shape and is fixedly attached to the cylindrical wall.

60. The culture vessel of claim 48, further comprising a gas exchange device in fluid communication with the pump, said gas exchange device introducing oxygen into and removing carbon dioxide from the fluid culture medium.

61. The culture vessel of claim 48, wherein the tubular vessel has a recession in the cylindrical wall adjacent for trapping bubbles in the fluid culture medium and a port adjacent the recession for removing trapped bubbles.

62. The culture vessel of claim 48, further comprising at least one sensor for monitoring the fluid culture medium passing through the growth chamber.

63. The culture vessel of claim 62, further comprising a microprocessor in communication with the at least one sensor, the microprocessor controlling the content, temperature and/or flow rate of the fluid culture medium.

* * * * *